US008129551B2

(12) United States Patent
Szul et al.

(10) Patent No.: US 8,129,551 B2
(45) Date of Patent: Mar. 6, 2012

(54) ALKYLENE OXIDE RECOVERY SYSTEMS

(75) Inventors: John F. Szul, Hurricane, WV (US);
James H. Mccain, Charleston, WV (US); Floyd L. Pfeffer, Midland, MI (US); Harvey E. Andresen, Luling, LA (US); Phillip R. Fairchild, Luling, LA (US); Kent E. Newman, Scott Depot, WV (US)

(73) Assignee: Dow Technology Investments LLC, Midland, MI (US)

( * ) Notice: Subject to any disclaimer, the term of this patent is extended or adjusted under 35 U.S.C. 154(b) by 439 days.

(21) Appl. No.: 12/460,810

(22) Filed: Jul. 24, 2009

(65) Prior Publication Data
US 2010/0029963 A1  Feb. 4, 2010

Related U.S. Application Data

(60) Provisional application No. 61/137,517, filed on Jul. 31, 2008, provisional application No. 61/137,494, filed on Jul. 31, 2008, provisional application No. 61/137,493, filed on Jul. 31, 2008, provisional application No. 61/137,514, filed on Jul. 31, 2008, provisional application No. 61/137,485, filed on Jul. 31, 2008.

(51) Int. Cl.
*C07D 301/32* (2006.01)
*B01D 3/38* (2006.01)
(52) U.S. Cl. .......................................... 549/541; 203/76
(58) Field of Classification Search .................... 549/54; 203/76
See application file for complete search history.

(56) References Cited

U.S. PATENT DOCUMENTS

| | | | |
|---|---|---|---|
| 2,615,901 A | 10/1952 | McClellan | |
| 2,697,104 A | 12/1954 | Lowe et al. | |
| 2,771,473 A | 11/1956 | Courter | |
| 2,775,600 A | 12/1956 | Maslan | |
| 2,815,650 A | 12/1957 | McIntire et al. | |
| 3,094,401 A | 6/1963 | Lidell | |
| 3,165,539 A | 1/1965 | Lutz | |
| 3,174,262 A | 3/1965 | Lutz | |
| 3,216,177 A | 11/1965 | Bracken et al. | |
| 3,398,062 A | 8/1968 | Tsao | |
| 3,418,338 A | 12/1968 | Gilman et al. | |
| 3,531,376 A | 9/1970 | Minoda et al. | |
| 3,729,899 A | 5/1973 | Cunningham | |
| 3,745,092 A | 7/1973 | Vanderwater | |
| 3,766,714 A | 10/1973 | Cunningham et al. | |
| 3,867,113 A | 2/1975 | Foster et al. | |
| 3,904,656 A | 9/1975 | Broz | |
| 3,948,621 A | 4/1976 | Cocuzza et al. |
| 3,964,980 A | 6/1976 | Ozero |
| 4,033,617 A | 7/1977 | Cocuzza et al. |
| 4,134,797 A | 1/1979 | Ozero |
| 4,597,833 A | 7/1986 | N'eel et al. |
| 4,845,296 A | 7/1989 | Ahmed et al. |
| 4,966,657 A | 10/1990 | Delannoy et al. |
| 4,983,260 A | 1/1991 | N'eel et al. |
| 5,233,060 A | 8/1993 | Pendergast et al. |
| 5,529,667 A | 6/1996 | Coffey |
| 6,080,897 A | 6/2000 | Kawabe |
| 6,123,812 A | 9/2000 | Bessling et al. |
| 6,437,199 B1 | 8/2002 | Oka et al. |
| 6,498,272 B1 | 12/2002 | Schröder et al. |
| 6,833,057 B1 | 12/2004 | Bessling et al. |
| 7,179,875 B2 | 2/2007 | Fuchs et al. |
| 2004/0236049 A1 | 11/2004 | Fuchs et al. |
| 2005/0103617 A1 | 5/2005 | Andreis et al. |
| 2005/0277778 A1 | 12/2005 | Viswanathan et al. |
| 2006/0264648 A1 | 11/2006 | Beekman et al. |

FOREIGN PATENT DOCUMENTS

| | | |
|---|---|---|
| CZ | 104663 | 8/1962 |
| DE | 1165567 | 3/1964 |
| DE | 199 24 533 | 11/2000 |
| DE | 19924533 | 11/2000 |
| DE | 101 38 150 | 2/2003 |
| DE | 10138150 | 2/2003 |
| EP | 0 181 273 | 5/1986 |
| EP | 0181273 | 5/1986 |
| FR | 1 330 900 | 5/1963 |
| FR | 1330900 | 5/1963 |
| FR | 2 851 564 | 8/2004 |
| FR | 2851564 | 8/2004 |
| GB | 564646 | 10/1944 |
| GB | 589547 | 6/1947 |
| JP | 54-16416 | 2/1979 |
| JP | 54016416 | 2/1979 |
| JP | 62-12770 | 1/1987 |
| JP | 62012770 | 1/1987 |
| WO | WO 03/055869 | 7/2003 |
| WO | WO 2004/056453 | 7/2004 |
| WO | WO 2006/120207 | 11/2006 |
| WO | WO 2009/094103 | 7/2009 |
| WO | WO 2009/105252 | 8/2009 |

OTHER PUBLICATIONS

International Search Report and Written Opinion from related PCT Application PCT/US 2009/004318, dated Jan. 22, 2010 (15 pgs).
Viera, G.A., et al. "Lessons Learned from the Ethylene Oxide Explosion at Seadrift, Texas". Chem Eng. Progress. 89 (8), pp. 66-75 (1993).

(Continued)

*Primary Examiner* — Bernard Dentz
(74) *Attorney, Agent, or Firm* — Brooks, Cameron & Huebsch, PLLC

(57) ABSTRACT

The invention relates to improved systems for recovery of alkylene oxide from feed streams containing the same in an alkylene oxide recovery column. The invention also relates to improved processes for recovery of alkylene oxide from feed streams containing the same in an alkylene oxide recovery column.

20 Claims, 5 Drawing Sheets

OTHER PUBLICATIONS

Wankat, P.C. et al. "Two-Feed Distillation: Same-Composition Feeds with Different Enthalpies" Ind. Eng. Chem. Res. 1993, 32, 3061-3067.

Cleveland et al. "Meteor Revolution" Hydrocarbon Engineering Oct. 2001 pp. 69-71.

Xiangyu, Z. "A Comparison of EO/EG Process Technologies" Sinopec Shanghai Engineering Co. Shanghai, 2006.

SIDE BY SIDE CONCEPT

CONCENTRIC CONCEPT

ALKYLENE OXIDE RECOVERY SYSTEMS

This application claims priority to U.S. Provisional Application 61/137,517 filed Jul. 31, 2008, the specification of which is incorporated herein by reference, and is co-filed with co-owned U.S. patent application Ser. No. 61/137,494, entitled "Alkylene Oxide Recovery Systems" filed on even date herewith; U.S. patent application Ser. No. 61/137,493, entitled "Alkylene Oxide Recovery Systems" filed on even date herewith; U.S. patent application Ser. No. 61/137,514, entitled "Alkylene Oxide Purification Processes and Systems" filed on even date herewith; and U.S. patent application Ser. No. 61/137,485, entitled "Alkylene Oxide Purification Systems" filed on even date herewith.

FIELD OF THE DISCLOSURE

Embodiments of the present disclosure relate to improved systems and processes for recovering alkylene oxide from feed streams containing the same.

BACKGROUND

Alkylene oxide such as ethylene oxide is typically produced in an oxidation reactor by a silver catalyzed, vapor phase, partial oxidation of ethylene with molecular oxygen which results in a gaseous reaction effluent. However, the gaseous reaction effluent can be extremely dilute with respect to the desired ethylene oxide content, containing for example, from about 0.3 mole percent to about 5 mole percent of ethylene oxide. In addition, the gaseous reaction effluent can further contain undesirable components such as acetaldehyde and formaldehyde that can be formed in the oxidation reactor or downstream to the oxidation reactor.

Recovery of the ethylene oxide from the gaseous reaction effluent can involve an initial water absorption step, followed by a stripping step, which is in turn followed by a reabsorption step. In some instances, each of the steps is carried out in separate distillation columns, which can lead to high equipment costs and safety concerns where areas of concentrated vapor phase or liquid phase ethylene oxide exist. One exemplary area where concentrated liquid phase ethylene oxide can exist is when vapor phase ethylene oxide coming out of the top of an ethylene oxide stripper is condensed, giving liquid ethylene oxide. The liquid ethylene oxide produced in the stripper can be transported to another piece of equipment to be further refined. However, handling and/or transporting concentrated ethylene oxide, for example, liquid ethylene oxide, can be dangerous due to the risk of contamination since contaminated liquid ethylene oxide can lead to a runaway polymerization which generates heat and can be explosively violent. As such, avoiding and/or alleviating the areas of concentrated and/or contaminated liquid ethylene oxide can increase safety in the recovery of ethylene oxide.

For applications requiring higher ethylene oxide product purity the ethylene oxide has to be further refined. Typically the ethylene oxide product recovered can undergo a number of distillation steps which can again adversely affect the production economics. Thus an improved system and process for recovery of alkylene oxide from an aqueous mixture containing ethylene oxide is desirable. An improved system for recovery of alkylene oxide may avoid or alleviate some of the issues presently associated with alkylene oxide recovery.

SUMMARY

In some embodiments, a process for the recovery of alkylene oxide is provided. The process includes introducing a feed stream containing alkylene oxide to a stripping section of an alkylene oxide recovery column. The alkylene oxide recovery column includes the stripping section and a reabsorption region. The process further includes stripping alkylene oxide from the feed stream to form a first gaseous portion in the stripping section. The first gaseous portion flows from the stripping section to the reabsorption region of the alkylene oxide recovery column. The reabsorption region further includes a first reabsorption section and a second reabsorption section. The first gaseous portion is partially condensed into a liquid reflux stream and an alkylene oxide rich vapor stream where the liquid reflux stream is in physical communication with the stripping section. The process further includes reabsorbing a first fraction of the alkylene oxide rich vapor stream in a first water stream to form a first aqueous solution in the first reabsorption section. The first reabsorption section includes a first take-off to remove the first aqueous solution from the first reabsorption section. The process further includes reabsorbing a second fraction of the alkylene oxide rich vapor stream in a second water stream to form a second aqueous solution in the second reabsorption section. The second reabsorption section includes a second take-off to remove the second aqueous solution from the second reabsorption section.

In another embodiment, a system for the recovery of alkylene oxide is provided. The system includes a stripping section located in an alkylene oxide recovery column to convert a portion of a feed stream to a gas phase portion. The gas phase portion of the feed stream includes alkylene oxide. The system further includes a condenser to partially condense the gas phase portion of the feed stream to produce an alkylene oxide rich vapor stream and a liquid reflux stream. The system further includes a first reabsorption section in the alkylene oxide recovery column to reabsorb in a first water stream a first fraction of the alkylene oxide from the alkylene oxide rich vapor stream to form a first aqueous solution. The first reabsorption section includes a first water inlet to provide the first water stream in the first reabsorption section. The system further includes a second reabsorption section in the alkylene oxide recovery column to reabsorb in a second water stream a second fraction of the alkylene oxide from the alkylene oxide rich vapor stream to form a second aqueous solution. The second reabsorption section includes a second water inlet to provide the second water stream in the second reabsorption section.

In various embodiments, a system for recovery of alkylene oxide is provided, where the alkylene oxide is ethylene oxide. The system includes a stripping section located in an alkylene oxide recovery column to convert a portion of a feed stream to a gas phase portion, where the gas phase portion of the feed stream includes alkylene oxide. The system further includes a condenser to partially condense the gas phase portion of the feed stream to produce an alkylene oxide rich vapor stream and a liquid reflux stream. The system further includes a first reabsorption section in the alkylene oxide recovery column to reabsorb in a first water stream a first fraction of the alkylene oxide from the alkylene oxide rich vapor stream to form a first aqueous solution. The first reabsorption section includes a first water inlet to provide the first water stream to reabsorb about 0.1 percent to about 15 percent of the alkylene oxide from the alkylene oxide rich vapor stream. The system further includes a second reabsorption section in the alkylene oxide recovery column to reabsorb in a second water stream a second fraction of the alkylene oxide from the alkylene oxide rich vapor stream to form a second aqueous solution. The second reabsorption section includes a second water inlet to provide the second water stream to reabsorb about 10 percent to about 80 percent of the alkylene oxide from the alkylene oxide rich vapor stream. The system further includes a third reabsorption section in the alkylene oxide recovery column to reabsorb in a third water stream a third fraction of the alkylene oxide from the alkylene oxide rich vapor stream to form a third aqueous solution. The third aqueous solution is substantially free of impurities.

DEFINITIONS

As used herein, the term "about" may not be limited to the precise value specified. In at least one instance, the variance indicated by the term "about" can be determined with reference to the precision of the measuring instrumentation.

As used herein a "separation stage" is defined as a volume, device or combination of devices in a distillation apparatus within or at which phases are brought into intimate contact, where mass transfer occurs between the phases tending to bring them to equilibrium, and where the phases can then mechanically separated. For the various embodiments, each tray of a tray tower and/or packing of a packed tower having a height equivalent to a theoretical plate ("HETP") is a separation stage, as these are the locations where fluids are brought into intimate contact, interphase diffusion occurs, and the fluids are separated. As such, the number of trays in a distillation apparatus can also be attributed to an equivalent number of separation stages that are obtained by using packing. For the various embodiments, the terms separation stage, tray and/or packing having a HETP can be used interchangeably, unless otherwise stated to the contrary.

As appreciated by one skill in the art, determining a number of equilibrium stages (theoretical trays) for use in a distillation apparatus can be calculated based on the material balances and equilibrium considerations of the compounds (e.g., ethylene oxide, water, and other compounds in liquid form) to be separated in the substance (e.g., the aqueous mixture of the present disclosure). The efficiency of the separation stage, and therefore the number of separation stages that are actually used, can be determined by the mechanical design used and the condition of operation for the distillation apparatus. For the various embodiments provided herein, the number of equilibrium stages (or theoretical trays) could be used in place of the number of separation stages provided in the present disclosure through the use of the efficiency of the separation stage of the distillation apparatus.

As used herein, the term "stripping portion" refers to a section in a column where one or more components of an aqueous solution are removed by being placed in contact with a gas stream that is insoluble in the aqueous solution or by heating the aqueous solution to cause a phase change of the one or more components that has to be removed.

As used herein, the term "reabsorption section" refers to a section of the column where components of a gas are removed by contacting the gas with a liquid that absorbs some components of the gas.

As used herein, the term "condenser" refers to a device that converts a portion of the vapor into a liquid.

As used herein, "a," "an," "the," "at least one," and "one or more" are used interchangeably. The terms "comprises" and variations thereof do not have a limiting meaning where these terms appear in the description and claims. Thus, for example, a stripping section located in an ethylene oxide recovery column to convert a portion of "a" feed stream to a gas phase portion can be interpreted to mean that the ethylene oxide recovery column includes "one or more" feed streams.

The term "and/or" means one, more than one, or all of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

BRIEF DESCRIPTION OF THE DRAWINGS

In the accompanying drawings, like characters represent like parts throughout the drawings, wherein.

DETAILED DESCRIPTION

Figure 1:
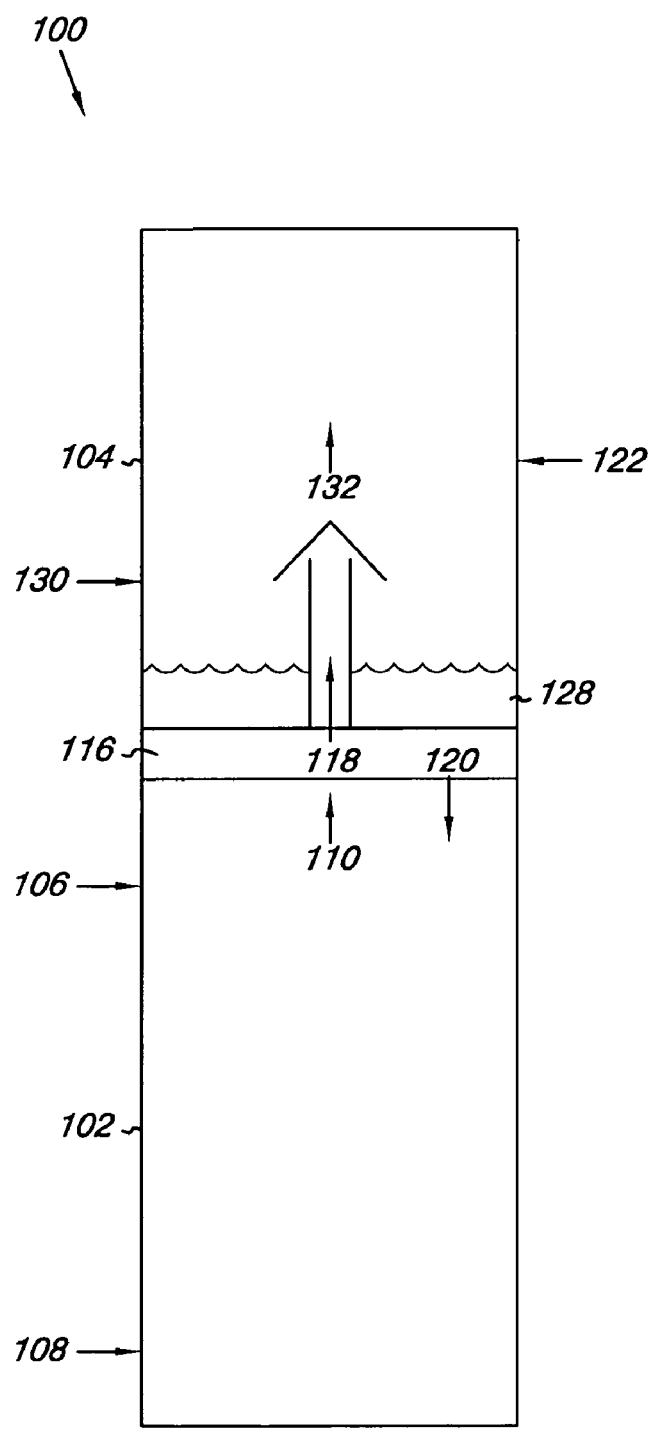
FIG. 1 shows a schematic representation of a system for recovery of alkylene oxide.

The conversion of alkylene (olefin), in particular ethylene, to alkylene oxide (olefin oxide), in particular ethylene oxide, is typically carried out in a catalyst containing reactor by continuously introducing a reactant stream containing ethylene and oxygen, or an oxygen containing gas, at a temperature of about 200 degrees Celsius (° C.) to about 300° C., and a pressure in a range of about 5 atmospheres (506 kilopascals (kPa)) to about 30 atmospheres (3,040 kPa) depending on the productivity desired. The residence time in large scale reactors can be on the order of about 0.1 seconds to about 5 seconds.

Typically, the per pass conversion of ethylene to ethylene oxide is low i.e., on the order of 1 percent or less. The gaseous reaction effluent thus formed contains dilute concentrations of ethylene oxide along with unreacted ethylene, unreacted oxygen, aldehydes, acidic impurities, nitrogen, argon, and carbon dioxide among other components. However, the ethylene oxide can be separated and recovered from the gaseous reaction effluent. To recover the ethylene oxide, the gaseous reaction effluent from the reactor can be scrubbed with an absorbent, such as water, to form an aqueous mixture containing ethylene oxide in an absorber column. The absorption of ethylene oxide in water from the gaseous reaction effluent recovers ethylene oxide from unreacted ethylene and/or oxygen and/or other gaseous components (e.g., carbon dioxide, nitrogen and argon) of the gaseous reaction effluent to a certain extent. The remaining gaseous materials can then be recycled as cycle gas to be mixed with the feedstock of ethylene and pure oxygen and fed to an ethylene oxide reactor for the production of ethylene oxide as gaseous reaction effluent.

In a typical ethylene oxide production unit, the ethylene oxide production processes can be interlinked with ethylene oxide recovery processes and in certain cases where the ethylene oxide production unit is operated along with downstream product manufacturing units such as, for example an ethylene glycol manufacturing unit, the ethylene oxide processes can be interlinked with ethylene glycol manufacturing processes to maximize energy utilization which in turn can lower production costs.

Alkylenes employed in embodiments of the present invention are characterized by the following structural formula (I):

(I)

where $R_1$ and $R_2$ are each individually selected from hydrogen and lower monovalent radicals, preferably $C_1$-$C_6$ alkyl radicals including methyl, ethyl, propyl, butyl and higher homologues having up to six carbon atoms. In some embodiments, $R_1$ and $R_2$ are each individually selected from hydrogen, methyl, ethyl and propyl. In one embodiment, both of $R_1$ and $R_2$ are hydrogen and the preferred alkylene is ethylene. In some embodiments, the alkylene is propylene, where $R_1$ is hydrogen and $R_2$ is methyl. The corresponding alkylene oxides produced are preferably characterized by the following structural formula (II):

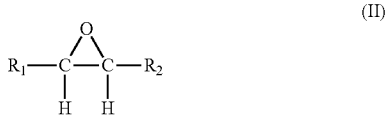

(II)

where $R_1$ and $R_2$ are identified herein in connection with the reactant alkylene. In some embodiments, the alkylene oxide is ethylene oxide (i.e., $R_1$ and $R_2$ are both hydrogen). In certain embodiments, the alkylene oxide is propylene oxide (i.e., $R_1$ is hydrogen and $R_2$ is methyl). Other exemplary alkylene oxides include oxides with the formula (II), where $R_1$ and $R_2$ are each individually selected from hydrogen and lower monovalent radicals, preferably $C_1$-$C_6$ alkyl radicals.

FIG. 1 illustrates a schematic representation of an ethylene oxide recovery column 100 for the recovery of ethylene oxide from a feed stream 106 containing ethylene oxide, the details of which may be found in the U.S. Provisional Application No. 61/137,494, entitled "Alkylene Oxide Recovery Systems" filed on the same date herewith, the contents of which are incorporated herein by reference. The ethylene oxide recovery column 100 includes a first stripping portion 102 and a reabsorption portion 104.

The alkylene oxide recovery column 200 includes a stripping section 202 located in the column 200 and a reabsorption region 204 above the stripping section 202. In certain embodiments, the stripping section 202 may be located at a lower half of the alkylene oxide recovery column 200 and the reabsorption region 204 may be located at an upper half of the alkylene oxide recovery column 200.

Briefly, in the first stripping portion 102, the feed stream 106 containing ethylene oxide is introduced. The feed stream 106 makes contact in a countercurrent fashion with a first gaseous stream 108 to convert a portion of the feed stream 106 to a gas phase portion 110. The gas phase portion 110 of the feed stream 106 flows from the stripping portion 102 to a condenser 116 to cool and partially condense the gas phase portion 110 to produce an ethylene oxide rich vapor stream 118 and a liquid reflux stream 120. The ethylene oxide rich vapor stream 118 flows from the condenser 116 to the reabsorption portion 104 of the column 100. The reabsorption portion 104 absorbs ethylene oxide from the ethylene oxide rich vapor stream 118 by contacting the ethylene oxide rich vapor stream 118 with a water stream 122 to form an aqueous solution 128. A steam stream 130 is provided in the reabsorption portion 104 to remove carbon dioxide and oxygen from the aqueous solution 128 as a light impurity fraction 134. The light impurity fraction 134 formed can be removed from an upper portion of the column 100.

The aqueous solution 128, in some embodiments is directed to a glycol unit for the conversion of ethylene oxide to ethylene glycol. In certain embodiments, the aqueous solution 128 may be sent to an ethylene oxide purification column for further removal of impurities.

Figure 2:
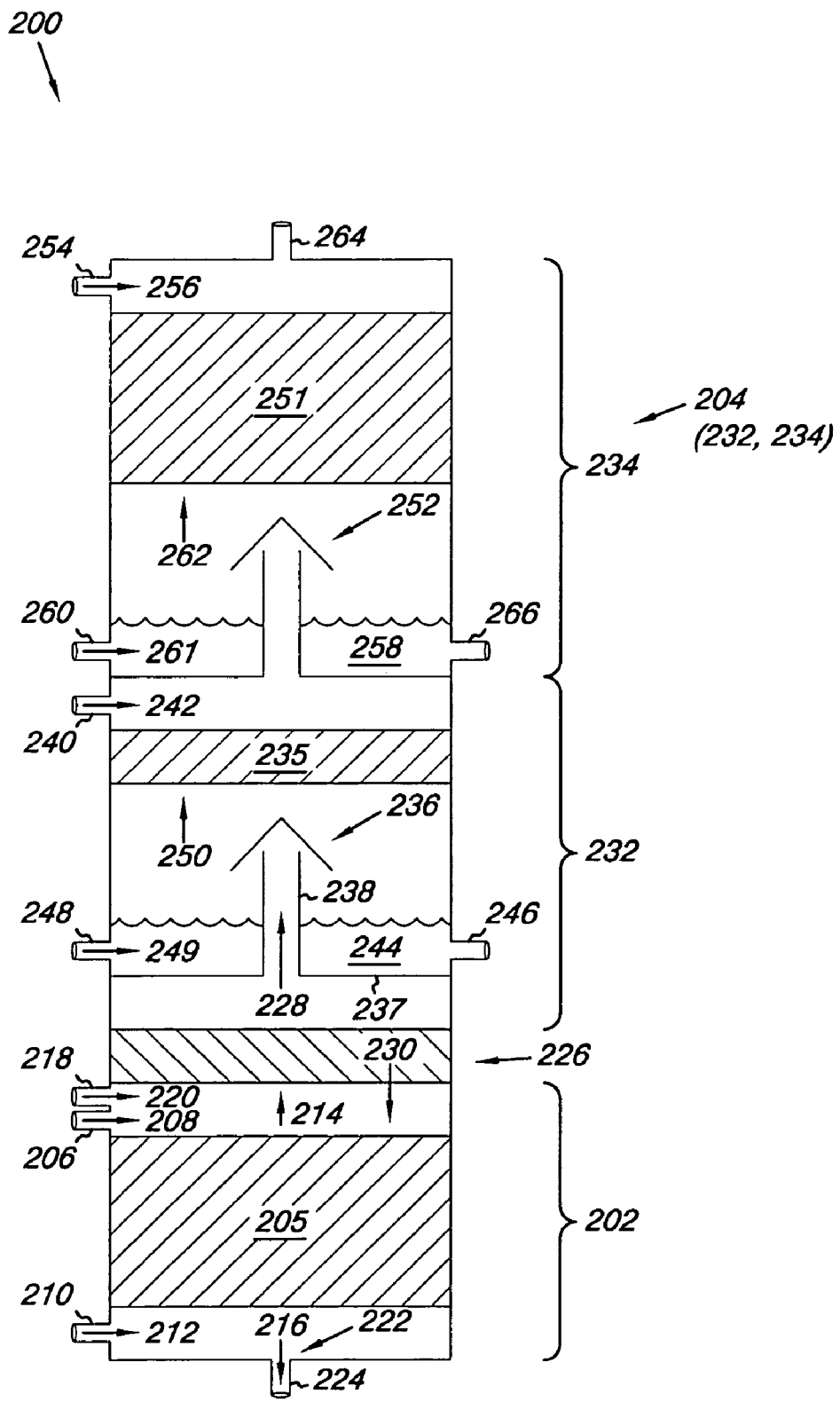
FIG. 2 illustrates an exemplary system for recovery of alkylene oxide in accordance with embodiments of the present invention.

FIG. 2 is an illustration of an alkylene oxide recovery column 200 according to embodiments of the present disclosure. The alkylene oxide recovery column 200 may be configured to be of a variety of shapes and orientations. In some embodiments, the alkylene oxide recovery column 200 can have a polygonal shape and can be oriented in a horizontal manner. The alkylene oxide recovery column 200 may be of a variety of sizes. For example, recovery column 200 having a cylindrical shape can have a diameter in a range of about 65 centimeters to about 6 meters, or more than about 6 meters, and a height in a range of about 6 meters to about 65 meters, or more than about 65 meters. As will be appreciated, the alkylene oxide recovery column 200 may be made of any material commonly used in making such columns, for example, the column can be made of steel. In some embodiments, the alkylene oxide recovery column 200 may be jacketed, wherein a space between the jacket and the column 200 may be flushed with an inert gas, for example carbon dioxide, nitrogen, and/or argon. The column having a jacket may provide protection against external sources of ignition which otherwise might initiate explosive decomposition of alkylene oxide. In the illustrated embodiment, the alkylene oxide recovery column 200 is a vertically oriented cylindrical column made of stainless steel.

The operating conditions within the recovery column 200 may be adjusted according to processing conditions. For example, the column 200 may be operated at a wide range of pressures, ranging from sub-atmospheric (i.e., vacuum), to near atmospheric, to super atmospheric. In practice, the general operating pressure of the column 200 can be selected during system design, although there is some flexibility to adjust the pressure of the column 200 during normal operation. The design operating pressure of the column 200 can range from about 60 kilopascal (kPa) to about 2,200 kPa, preferably from about 80 kPa to about 1,100 kPa, and more preferably from about 100 kPa to about 450 kPa.

In addition, there can be a gradient in pressure across the column 200, with the highest pressure in the stripping section 202 and the lowest pressure in the reabsorption region 204, as discussed herein. This gradient may be a gradual change across the column 200 and/or various sections of the column 200, or may be an abrupt pressure change. As one skilled in the art will appreciate, the pressure drop can be primarily generated across trays and/or packing in the stripping section 202, as discussed further herein, across the mid-column condenser, as discussed herein, and/or across trays and/or packing in the reabsorption region 204, as discussed further herein. In addition, the pressure drop can be influenced by design and operational factors, such as vapor flux, liquid flux, the number of trays and/or packing height, the choice of packing, and/or condenser design, among other factors. The pressure gradient in the column 200 can range from about 1 kPa to about 1,000 kPa, preferably from about 3 kPa to about 500 kPa, and more preferably from about 5 kPa to about 300 kPa.

The alkylene oxide recovery column 200 may also be operated at a wide range of temperatures. In practice, the operating temperature of the column can be selected during system design, although there can be significant variation in the column temperature during operation. In addition, there can be a temperature gradient present in the column 200, with the highest temperature in the stripping section 202 and the lowest temperature in the reabsorption region 204. This gradient may be a gradual change across the column and/or various sections of the column, or may be an abrupt temperature change. The operating temperature of the stripping section 202 can range from about 40° C. to about 200° C., preferably from about 60° C. to about 160° C., and more preferably from about 80° C. to about 140° C. The operating temperature of the reabsorption section 204 can range from about 10° C. to about 120° C., preferably from about 20° C. to about 100° C., and more preferably from about 25° C. to about 80° C.

As can be appreciated by one skilled in the art, the operating temperature of the column 200, the operating pressure of the column 200, and the composition of the feed stream 206, discussed herein, can all be highly interdependent. Also, certain sections of the column 200 can be impacted by other variables, such as the reabsorption water temperature, desired reflux ratio, pressure drop, the presence of other feed inlets and/or outlets, and/or the presence of auxiliary heaters and/or coolers. In design and operation, these variables can be optimized to provide a balance between the operating cost of the stripping section 202, the operating cost of the reabsorption section 204, and the overall column 200 capital cost. For instance, the stripping section 202 can have the lowest operating cost when run at lower pressure; however, the reabsorption section 204 can have the lowest operating costs when operated at high pressure. Other factors may also impact the chosen system operating pressure, such as column cost (e.g., higher pressure columns lead to more capital cost) or heat source availability (e.g., the heat source is required to drive the stripping section 202 to a certain temperature). In addition, often the optimum economic balance is related to heat integration requirements or other integrations requirements with other parts of the plant.

In some embodiments, the stripping section 202 can be operated at a pressure in a range from about 130 kPa to about 150 kPa and a temperature in a range of from about 100° C. to about 120° C., while the reabsorption portion 204 can be operated at a pressure in a range of from about 110 kPa to about 130 kPa and a temperature in a range of from about 30° C. to about 50° C.

The column 200 of the present disclosure can be operated with distillation trays (plates), packing, or a combination of distillation trays and packing. The distillation trays can be of any type of plate commonly found in distillation columns, such as sieve plates, bubble-cap plates or valve plates, among others. In some embodiments, the distance between each tray can vary. In addition, in embodiments using packing, the packing material can be random dumped packing such as, for example, Raschig rings, Pall rings, or Bialecki rings in metal or ceramic. The packing material can also be structured sheet-metal packing such as those known and commercially available for example under the designations Gempak® (Koch-Glitsch, L P, Dallas, Tex., U.S.A) and/or Mellapak® (Gebr. Sulzer, Winterthur, Switzerland).

In embodiments where random packing is employed, the total required height of packing to provide the required number of separation stages can be determined by multiplying the number of calculated equilibrium stages by the Height Equivalent to a Theoretical Plate, or HETP. The HETP is a value of the height of packing that will give the same separation as an equilibrium stage. As known to one skilled in the art, the HETP can vary depending on the type of packing selected.

In some embodiments, the total height of packing can be split into one or more zones with vapor-liquid redistributors in between the zones, for example, to accommodate height limitations due to packing structural integrity or to accommodate feed streams or product streams. In some embodiments, packing may offer the advantage of a lower pressure drop as compared to trays, although consideration must also be given to the cost difference arising from the choice of trays versus packing.

The stripping section 202 has a zone 205. In some embodiments, the stripping section 202 of the column 200 can be operated in such a way that the zone 205 includes between 4 and 14 separation stages, preferably between 6 and 12 separation stages, and more preferably between 7 and 11 separation stages. As such, the stripping section 102 can include about 6 to about 25 separation stages. In some embodiments, when trays are used the distance between each tray can vary, where the distance between each tray is optimized for the best separation of the feed stream 106 components at the specific temperature and pressure of each tray.

As known to those skilled in the art, the design and operation of the stripping section 202 will depend on the composition of a feed stream as well as the composition of desired products, among other things. In some instances, for example, with a binary component feed stream, analytical methods such as the McCabe Thiele method or the Fenske equation can be used. For multi-component feed stream, simulation models can be used for both design (e.g., to determine the number of equilibrium stages needed in order to achieve the desired separation) and operation (e.g., to determine the optimum operating conditions). In addition, once the number of equilibrium stages is determined, one skilled in the art can use routine experimentation to determine the actual number of separation stages (e.g., the actual number of trays or height of packing) to use in a column to achieve the desired separation.

The stripping section 202 can have a number of components including inlets, and outlets. In the illustrated embodiment, a feed inlet 206 is provided at an upper portion of the stripping section 202 to introduce a feed stream 208 into the stripping section 202.

The feed stream 208 includes alkylene oxide and water. Non-limiting examples of other compounds in the feed stream 208 include methane, carbon dioxide, oxygen, and/or alkylene, among others. In some embodiments, the composition of the feed stream 208 is about 1 weight percent to about 5 weight percent alkylene oxide, 0 weight percent to about 0.03 weight percent alkane (e.g., methane), about 0 weight percent to about 0.03 weight percent carbon dioxide, about 0 weight percent to about 0.015 weight percent oxygen, about 0 weight percent to about 0.06 weight percent alkylene with the remaining portion being made up of water. In one embodiment, the composition of the feed stream 208 is about 3 weight percent ethylene oxide, about 0.02 weight percent methane, about 0.02 weight percent carbon dioxide, about 0.01 weight percent oxygen, about 0.04 weight percent ethylene with the remaining portion being made up of water. The feed stream 208 may further contain impurities namely, chlorine containing organic compounds and oxygenated hydrocarbons. In certain embodiments, the feed stream 208 is of two phases, a liquid phase and a vapor phase.

The stripping section 202 includes a stripping stream inlet 210 to introduce a stripping gas 212 in the stripping section 202. In one embodiment, the stripping stream inlet 210 can be located at a lower portion of the stripping section 202 to contact the feed stream 208 in a counter current fashion with the stripping gas 212. In one embodiment, the stripping gas 212 is steam. In some embodiments, stripping gas can be generated internally in the stripping section 202. For example, steam can be generated within the stripping section 202 by making use of a heating mechanism placed internally or externally to the column 200. The stripping gas 212 strips alkylene oxide from the feed stream 208 to form a gas phase portion 214 containing alkylene oxide and an impurities fraction 216 that flows to the lower portion of the stripping section 202. The impurities fraction 216, in some embodiments, can also contain water and alkylene oxide and can be sent to an absorber column interlinked with the column 200 to further absorb alkylene oxide. In certain embodiments, the absorbed alkylene oxide can be brought back to the column 200 with the feed stream 208. In some embodiments, the alkylene oxide in the impurities fraction 216 routed to the absorber column can be in a range of about zero to about one thousand mole parts per million.

The stripping section 202 can further include at least one inlet to introduce at least one input stream containing alkylene or alkylene oxide or both from an alkylene oxide pre-recovery or post-recovery process to maximize the efficiency as well as the economics of alkylene oxide production and recovery. As discussed earlier, the recovery column 200 can be part of the alkylene oxide-glycol manufacturing unit including alkylene oxide production, concentration, purification and optionally glycol formation. The term "alkylene oxide production processes", as used herein, and hereafter, refers to alkylene oxide production, recovery, and glycol production processes, unless otherwise specified. The at least one input stream can be originated at any of the alkylene oxide production processes. For example, in one embodiment, the alkylene oxide production process can include a carbon dioxide absorption step. The carbon dioxide absorption is typically carried out in a carbon dioxide absorber column where a gas recycle stream of carbon dioxide containing alkylene oxide or unreacted alkylene, among others, are absorbed in an absorbing solution such as aqueous potassium carbonate. The absorbing solution may absorb gases such as alkylene oxide or unreacted alkylene from the gas recycle stream of carbon dioxide. In embodiments including the carbon dioxide absorption step, a flash tank may be further employed, where the majority of the absorbed gases are flashed off and collected and returned to at least one process linked to an alkylene oxide production process. In some embodiments, the collected gases can be routed to the stripping section 202 where the impurities can be washed off. Other input streams may include streams from an alkylene oxide purification vent, an alkylene oxide clean-up header, and/or an alkylene oxide storage tank scrubber water, among others. In one embodiment, the at least one input stream is stripped in the stripping section 202 with the feed stream 208.

A first outlet 224 is provided at the lower portion of the stripping section 202. In some embodiments, the first outlet 224 is used to remove the impurities fraction 216. In certain other embodiments, the first outlet 224 is used to remove the impurities fraction 216 and the neutralized solution 222 from the recovery column 200.

During operation, the gas phase portion 214 of the feed stream 208 flows from the stripping section 202 to a condenser 226 to cool and partially condense the gas phase portion 214 to produce an alkylene oxide rich vapor stream 228 and a liquid reflux stream 230. The liquid reflux stream 230 is in physical communication with the stripping section 202. The gas phase portion 214 of the feed stream 208, in one embodiment, is at a temperature of about 80° C. to about 110° C. while entering the condenser 226. In certain other embodiments, the gas phase portion 214 can be at a temperature of about 90° C. to about 100° C.

In some embodiments, the condenser 226 can include, for example, a cooling water stream flowing countercurrent with the flow of the gas phase portion 214 to cool and partially condense the gas phase portion 214. In FIG. 2, the condenser 226 is integral to the column 200 and is located above the stripping section 202. In some embodiments, the condenser 226 can be external to the column 200 and in series with the stripping section 202. In some embodiments, the condenser 226 is a reflux condenser and the condenser 226 can return condensed vapors directly to the stripping section 202, while non-condensable gases (for e.g., alkylene oxide rich vapor stream) pass through the condenser 226. In some embodiments, a portion of heat recovered from the condenser 226 can be usefully employed in other parts of the alkylene oxide recovery column processes and/or in other parts of the alkylene oxide production unit.

The alkylene oxide rich vapor stream 228 passes from the condenser 226 to the reabsorption region 204, where the reabsorption region 204 includes a first reabsorption section 232 and a second reabsorption section 234. The alkylene oxide rich vapor stream 228 from the condenser 226 enters the first reabsorption section 232 at a lower portion of the first reabsorption section 232.

The first reabsorption section 232, as illustrated, can have a zone 235, where the zone 235 includes separation stages (e.g., trays, dumped packing, structured packing or a mixture of trays and packing) as discussed with reference to the zone 205 of the stripping section 202. In some embodiments, the zone 235 can between 1 and 10 separation stages, preferably between 1 and 8 separation stages, and most preferably between 1 and 6 separation stages.

In some embodiments, the temperature in the first reabsorption section 232 is in the range of about 10° C. to about 120° C., preferably from about 20° C. to about 100° C., and more preferably from about 25° C. to about 80° C. The pressure in the first reabsorption section 232 can be in the range of about 60 kilopascal (kPa) to about 2,200 kPa, preferably from about 80 kPa to about 1,100 kPa, and more preferably from about 100 kPa to about 450 kPa.

In some embodiments, the first reabsorption section 232 can include a first chimney tray 236 located at the lower portion of the first reabsorption section 232. As used herein, a "chimney tray" is a tray designed in such a way that it will allow vapor (e.g., alkylene oxide rich vapor stream) to rise through it, but prevents liquid from passing down through it by accumulating the down flowing liquid over a collection tray 237. For the various embodiments, other tray designs, other devices and/or constructions that allows vapor to pass up and that prevents liquid from passing down may also be used. As will be appreciated, the chimney tray 236 may additionally enhance distribution of an up-flowing vapor (for e.g., alkylene oxide rich vapor stream) through the column, where the column may contain trays, dumped packing, structured packing or a mixture of trays and packing. In some embodiments, the chimney tray can be a solid collection tray 237 made of metal with a standpipe 238, topped by a hat 239 to keep liquid from raining down through the standpipe 238. A stand pipe 238, as used herein, is an open pipe which extends through the chimney tray 236 till a distance above the collection tray 237 so that liquid can stay and accumulate over the collection tray 237. As used herein, the term "hat" refers to a cover that is connected to the standpipe 238 to allow vapor to flow up and out of the standpipe, while preventing liquid from entering the standpipe from sections of the column 200 above it. As will be appreciated, the chimney tray 236 can be designed to overflow the collected liquid back into the stripping section 202 via the standpipe 238 during upset conditions, where the term "upset condition" is defined as the condition in which there is a disturbance or deviation from normal functioning of the process. In embodiments where the zone 235 of the first reabsorption section 232 includes trays, packing or a mixture of trays and packing, the chimney tray 236 can be designed such that the top of the standpipe 238 extends past some of the equilibrium stages in the first reabsorption section 232 of the column 200. As illustrated in FIG. 2, the alkylene oxide rich vapor stream 228 can enter the first reabsorption section 232 by passing through the first chimney tray 236.

A first water inlet 240 is provided in the first reabsorption section 232 to introduce a first water stream 242. The first water stream 242, in one embodiment is process water or raw water. In some embodiments, the first water stream 242 can be a recycle stream containing water from any one or more of the alkylene oxide production processes. The first water inlet 240, in some embodiments, is provided at an upper portion of the first reabsorption section 232.

The first water stream 242 reabsorbs a first fraction of alkylene oxide from the alkylene oxide rich vapor stream 228 to form a first aqueous solution 244 that is accumulated over the collection tray 237 of the first chimney tray 236. Hereinafter, for ease of convenience, the percentage of reabsorption of alkylene oxide from the alkylene oxide rich vapor stream 228 will be expressed with reference to the alkylene oxide rich vapor stream 228 exiting the condenser 226. As will be appreciated, reabsorbing the first fraction of the alkylene oxide rich vapor stream 228 to form the first aqueous solution 244 can occur by contacting a volume of first water stream 242 sufficient enough to reabsorb the first fraction. Other factors may contribute to the reabsorption of the first fraction of alkylene oxide from the alkylene oxide rich vapor stream 228 such as the concentration of alkylene oxide in the alkylene oxide rich vapor stream 228 and the temperature of the first water stream 242. According to embodiments of the present invention, reabsorbing the first fraction of the alkylene oxide rich vapor stream 228 in the first reabsorption section 232 includes reabsorbing about 0.1 percent to about 15 percent of the alkylene oxide from the alkylene oxide rich vapor stream 228. In particular embodiments, reabsorbing the first fraction of the alkylene oxide rich vapor stream 228 in the first reabsorption section 232 includes reabsorbing about 1 percent to about 10 percent of the alkylene oxide from the alkylene oxide rich vapor stream 228. As will be appreciated, reabsorbing the first fraction of alkylene oxide from the alkylene oxide rich vapor stream 228 can reabsorb aldehydic impurities that may be present in the alkylene oxide rich vapor stream 228. In some embodiments, about 20 percent, or more than about 20 percent of the aldehydic impurities present in the alkylene oxide rich vapor stream 228 are reabsorbed as the first fraction. In certain embodiments, about 20 percent to about 40 percent of the aldehydic impurities present in the alkylene oxide rich vapor stream 228 are reabsorbed as the first fraction. In one embodiment, about 40 percent to about 60 percent of the aldehydic impurities present in the alkylene oxide rich vapor stream 228 are reabsorbed as the first fraction. Non-limiting examples of aldehydic impurities include acetaldehyde and formaldehyde.

In some embodiments, the first aqueous solution 244 has a composition of alkylene oxide in the range of about 0.5 mole percent to about 20 mole percent, acetaldehyde in the range of about 0 mole parts per million (ppm) to about 5,000 mole ppm, and formaldehyde in the range of about 0 mole ppm to about 10,000 mole ppm. In certain embodiments, the concentration of each of acetaldehyde and formaldehyde is less than about 1 mole ppm in the first aqueous solution 244. The first aqueous solution 244 may further contain compounds that may be typically used and/or formed during alkylene oxide production processes such as chlorine containing organic compounds and oxygenated hydrocarbons.

The first reabsorption section 232 can include a first take-off 246 located in the first reabsorption section 232 to remove the first aqueous solution 244 from the first reabsorption section 232. In certain embodiments, the first take-off 246 can be located at a side wall of the first reabsorption section 232. In one embodiment, the first take-off 246 is in physical communication with a glycol production unit to transfer the first aqueous solution 244 from the first reabsorption section 232 to the glycol production unit. The "glycol production unit" as used herein, refers to a subsidiary glycol production unit designed to handle higher levels of impurities in the first aqueous solution as compared to, for example, a main glycol unit where the majority of the glycol is manufactured. In some embodiments, the glycol production unit can be independent of the main glycol unit. In certain embodiments, the glycol production unit can be interlinked with the main glycol unit. In certain embodiments, the first take-off 246 is in physical communication with an alkylene oxide purification unit to transfer the first aqueous solution 244 from the first reabsorption section 232 to the alkylene oxide purification unit. The alkylene oxide purification unit can further refine the first aqueous solution 244 to remove impurities such as aldehydic impurities (namely, acetaldehyde and formaldehyde) and/or light gases (namely, carbon dioxide and oxygen).

In the illustrated embodiment of FIG. 2, the first reabsorption section 232 has a first gaseous stream inlet 248 to introduce a first gaseous stream 249 in the first reabsorption section 232. In some embodiments, the first gaseous stream 249 includes steam. In certain embodiments, the first gaseous stream 249 is an inert gas such as methane or nitrogen. The first gaseous stream 249 can remove light gases such as carbon dioxide and oxygen from the first aqueous solution 244 to form a first light impurities fraction 250. As will be appreciated, the first light impurities fraction 250 flows upward with the alkylene oxide rich vapor stream 228 that has not been reabsorbed in the first reabsorption section 232 to the second reabsorption section 234.

The second reabsorption section 234, as illustrated, can have a zone 251, where the zone 251 includes separation stages (e.g., trays, dumped packing, structured packing or a mixture of trays and packing) as discussed previously with reference to the zones 205, 235 of the stripping section 202 and the first reabsorption section 232, respectively. In some embodiments, the second reabsorption section 234 can be configured in such a way as to include between 2 and 10 separation stages, preferably between 3 and 9 separation stages, and more preferably between 4 and 8 separation stages.

The temperature in the second reabsorption section 234, in some embodiments is in the range of about 10° C. to about 120° C., preferably from about 20° C. to about 100° C., and more preferably from about 25° C. to about 80° C. The pressure in the second reabsorption section 234 can be in the range of about 60 kilopascal (kPa) to about 2,200 kPa, preferably from about 80 kPa to about 1,100 kPa, and more preferably from about 100 kPa to about 450 kPa.

The alkylene oxide rich vapor stream 228 exiting the first reabsorption section 232 flows to a lower portion of the second reabsorption section 234. In some embodiments, the second reabsorption section 234 has a second chimney tray 252. As described earlier with reference to the first chimney tray 236, the second chimney tray 252 may allow vapors (e.g., alkylene oxide rich vapor stream 228) to pass through it while preventing liquid from raining down through it to the first reabsorption section 232. As discussed herein, other devices and/or constructions that allows vapor to pass up and that prevents liquid from passing down may also be used in place of the chimney tray. The alkylene oxide rich vapor stream 228 that flows into the second reabsorption section 234 is without the first fraction of alkylene oxide that is reabsorbed in the first reabsorption section 232. In embodiments where the first light impurities fraction 250 is formed in the first reabsorption section 232, the first light impurities fraction 250 flows to the second reabsorption section 234 along with the alkylene oxide rich vapor stream 228.

A second water inlet 254 can be provided in the second reabsorption section 234 to introduce a second water stream 256 in the second reabsorption section 234. In some embodiments, the second water stream 256 and the first water stream 242 are both sourced from the same water feed. In one embodiment, the second water stream 256 is a stream of process water or raw water. In some embodiments, the second water stream 256 can be a recycle stream from any one or more of the alkylene oxide production processes. The second water inlet 254, in some embodiments, is provided at an upper portion of the second reabsorption section 234.

The second water stream 256 reabsorbs a second fraction of the alkylene oxide from the alkylene oxide rich vapor stream 228 to form a second aqueous solution 258 that is collected on the second chimney tray 252. According to embodiments of the present invention, reabsorbing the second fraction of alkylene oxide from the alkylene oxide rich vapor stream 228 in the second reabsorption section 234 includes reabsorbing more than about 10 percent of the alkylene oxide from the alkylene oxide rich vapor stream 228. As will be appreciated, substantially all of the alkylene oxide from the alkylene oxide rich vapor stream 228 that has not been reabsorbed in the first reabsorption section 232 is reabsorbed as the second fraction in the second reabsorption section 234. As used herein, and hereinafter, the term "substantially all" refers to about 98 percent or more than about 98 percent of the alkylene oxide from the alkylene oxide rich vapor stream 228.

In some embodiments, reabsorbing the second fraction from the alkylene oxide rich vapor stream 228 includes providing a volume of the second water stream 256. In one embodiment, reabsorbing the first fraction from the alkylene oxide rich vapor stream 228 includes providing about 0.1 percent to about 30 percent of a combined volume of the volume of the first water stream 242 and the volume of the second water stream 256. In some embodiments, reabsorbing the first fraction from the alkylene oxide rich vapor stream 228 includes providing about 0.1 percent to about 20 percent of the combined volume of the first water stream 242 and the second water stream 256.

In the illustrated embodiment of FIG. 2, the second reabsorption section 234 has a second gaseous stream inlet 260 to provide a second gaseous stream 261 to remove light gases such as carbon dioxide and oxygen from the second aqueous solution 258 to form a second light impurities fraction 262. In some embodiments, the second light impurities fraction 262 that is formed in the second reabsorption section 234 and the first light impurities fraction 250 that is formed in the first reabsorption section 232 flow upward to the upper portion of the column 200. As illustrated in the FIG. 2, a second outlet 264 is provided on the upper portion of the column 200 in the second reabsorption section 234 to remove the first light impurities fraction 250 and the second light impurities fraction 262. In some embodiments, components of alkylene oxide rich vapor stream 228 that are not reabsorbed at the first reabsorption section 232 and/or the second reabsorption section 234 are removed through the second outlet 264 and can include components such as steam.

The second reabsorption section 234 can additionally include a second take-off 266 located in the second reabsorption section 234 to remove the second aqueous solution 258. In certain embodiments, the second take-off 266 can be located at a side wall of the second reabsorption section 234. In some embodiments, the second take-off 266 is in physical communication with a downstream product manufacturing unit, for example, the main glycol unit to transfer the second aqueous solution 258 from the second reabsorption section 234 to the main glycol unit. In certain embodiments, the second take-off 266 is in physical communication with an alkylene oxide purification unit to transfer the second aqueous solution 258 from the second reabsorption section 234 to the alkylene oxide purification unit for applications requiring higher purity of the alkylene oxide. The alkylene oxide purification unit can further refine the second aqueous solution 258 to remove impurities such as aldehydes and/or light gases. In certain other embodiments, the second take-off 266 is in physical communication with an alkylene oxide storage tank to store alkylene oxide.

In some embodiments, the concentration of alkylene oxide in the second aqueous solution 258 is less than about 10 mole percent. In certain embodiments, the concentration of ethylene oxide in the second aqueous solution 258 is about 1 mole percent to about 10 mole percent. In one embodiment, the second aqueous solution 258 is substantially free of impurities. As used herein, and hereinafter, the term "substantially free" refers to about or less than about 10 mole ppm of at least one of acetaldehyde and formaldehyde.

An unexpected result of the illustrated embodiment of FIG. 2 is the removal of aldehydic impurities to a certain extent at the first reabsorption section. A benefit of this unexpected result is that the impurities are reduced at the first reabsorption section and the resultant stream from the second reabsorption section (for example, the second aqueous solution) can be sent directly to the main glycol unit.

Figure 3:
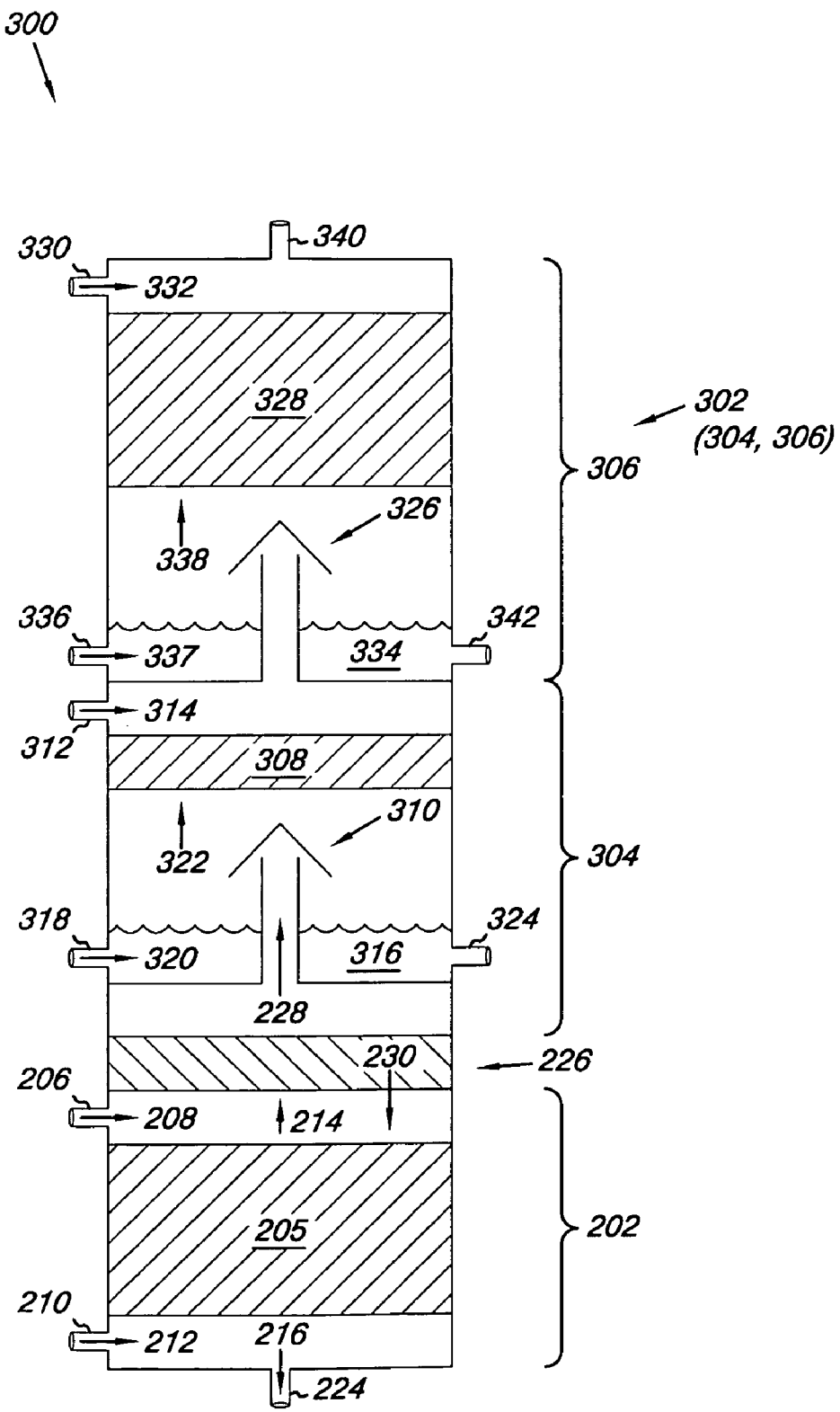
FIG. 3 illustrates an exemplary system for recovery of alkylene oxide in one embodiment of the present invention.

An alkylene oxide recovery column 300, in accordance with embodiments of the present disclosure is illustrated in FIG. 3. The stripping section 202 and the condenser 226 of the recovery column 300 are as described previously with reference to the recovery column 200 of FIG. 2.

The alkylene oxide rich vapor stream 228 exiting the condenser 226 enters a lower portion of a reabsorption region 302 of the column 300. The reabsorption region 302 includes a first reabsorption section 304 and a second reabsorption section 306.

The first reabsorption section 304, as illustrated in FIG. 3, can have a zone 308, where the zone 308 includes separation stages (e.g., trays, dumped packing, structured packing or a mixture of trays and packing). In this embodiment, the first reabsorption section 304 is configured to include between 2 and 10 separation stages, preferably between 3 and 9 separation stages and most preferably between 4 and 8 separation stages.

The temperature of the first reabsorption section 304, in some embodiments is in the range of about 10° C. to about 120° C., preferably from about 20° C. to about 100° C., and more preferably from about 25° C. to about 80° C. The pressure in the first reabsorption section 304 can be in the range of about 60 kilopascal (kPa) to about 2,200 kPa, preferably from about 80 kPa to about 1,100 kPa, and more preferably from about 100 kPa to about 450 kPa.

In some embodiments, the first reabsorption section 304 can include a first chimney tray 310 located at a lower portion of the first reabsorption section 304. As illustrated in FIG. 3, the alkylene oxide rich vapor stream 228 enters the first reabsorption section 304 through the first chimney tray 310.

A first water inlet 312 is provided in the first reabsorption section 304 to introduce a first water stream 314. The first water stream 314 reabsorbs a first fraction of alkylene oxide from the alkylene oxide rich vapor stream 228 to form a first aqueous solution 316 that is collected on the first chimney tray 310. As will be appreciated, reabsorbing the first fraction of alkylene oxide from the alkylene oxide rich vapor stream 228 to form the first aqueous solution 316 can occur by contacting a volume of the first water stream 314 sufficient enough to reabsorb the first fraction. According to embodiments of the present disclosure, reabsorbing the first fraction of alkylene oxide from the alkylene oxide rich vapor stream 228 in the first reabsorption section 304 includes reabsorbing about 0.1 percent to about 80 percent of the alkylene oxide from the alkylene oxide rich vapor stream 228. In particular embodiments, reabsorbing the first fraction of alkylene oxide from the alkylene oxide rich vapor stream 228 in the first reabsorption section 304 include reabsorbing about 1 percent to about 60 percent of the alkylene oxide from the alkylene oxide rich vapor stream 228. As will be appreciated, reabsorbing the first fraction of alkylene oxide from the alkylene oxide rich vapor stream 228 can reabsorb aldehydic impurities that may be present in the alkylene oxide rich vapor stream 228. In some embodiments, about 20 percent, or more than about 20 percent of the aldehydic impurities present in the alkylene oxide rich vapor stream 228 are reabsorbed as the first fraction. In certain embodiments, about 20 percent to about 40 percent of the aldehydic impurities present in the alkylene oxide rich vapor stream 228 are reabsorbed as the first fraction. In one embodiment, about 40 percent to about 90 percent of the aldehydic impurities present in the alkylene oxide rich vapor stream 228 are reabsorbed as the first fraction. Non-limiting examples of aldehydic impurities include acetaldehyde and formaldehyde.

In FIG. 3, the first reabsorption section 304 has a first gaseous stream inlet 318 to introduce a first gaseous stream 320 to remove light gases such as carbon dioxide and oxygen from the first aqueous solution 316 to form a first light impurities fraction 322. As will be appreciated, the first light impurities fraction 322 flows upward with the alkylene oxide rich vapor stream 228 that has not been reabsorbed in the first reabsorption section 304 to the second reabsorption section 306.

In one embodiment, the first aqueous solution 316 has a composition of alkylene oxide in the range of about 0.5 mole percent to about 10 mole percent, acetaldehyde in the range of about 0 mole ppm to about 5,000 mole ppm and formaldehyde in the range of about 0 mole ppm to about 5,000 mole ppm. In certain embodiments, the concentration of each of acetaldehyde and formaldehyde is less than about 1 mole ppm in the first aqueous solution 316. The first aqueous solution 316 may further contain compounds that may be typically used and/or formed during alkylene oxide production processes such as chlorine containing organic compounds and oxygenated hydrocarbons.

The first reabsorption section 304 can include a first take-off 324 located in the first reabsorption section 304 to remove the first aqueous solution 316. In certain embodiments, the first take-off 324 can be located at a side wall of the first reabsorption section 304. In some embodiments, the first take-off 324 is in physical communication with a main glycol unit to transfer the first aqueous solution 316 from the first reabsorption section 304 to the main glycol unit. In certain embodiments, the first take-off 324 is in physical communication with an alkylene oxide purification unit to transfer the first aqueous solution 316 from the first reabsorption section 304 to the alkylene oxide purification unit. The alkylene oxide purification unit can further refine the first aqueous solution 316 to remove and/or reduce impurities such as aldehydic impurities (namely, acetaldehyde and formaldehyde) and/or light gases (namely, carbon dioxide and oxygen). In some embodiments, the alkylene oxide rich vapor stream 228 that has not been reabsorbed in the first reabsorption section 304 flows to a lower portion of the second reabsorption section 306 through a second chimney tray 326.

In some embodiments, the temperature in the second reabsorption section 306 is in the range of about 10° C. to about 120° C., preferably from about 20° C. to about 100° C., and more preferably from about 25° C. to about 80° C. The pressure in the second reabsorption section 306 can be in the range of about 60 kilopascal (kPa) to about 2,200 kPa, preferably from about 80 kPa to about 1,100 kPa, and more preferably from about 100 kPa to about 450 kPa.

In some embodiments, the second reabsorption section 306 can have a zone 328 and the zone 328 includes separation stages (e.g., trays, dumped packing, structured packing or a mixture of trays and packing). In certain embodiments, the second reabsorption section 306 can be operated in such a way as to include between 2 and 10 separation stages, preferably between 3 and 9 separation stages, and most preferably between 4 and 8 separation stages.

A second water inlet 330 is provided in the second reabsorption section 306 to introduce a second water stream 332. The second water stream 332 reabsorbs a second fraction of the alkylene oxide from the alkylene oxide rich vapor stream 228 to form a second aqueous solution 334. According to embodiments of the present invention, reabsorbing the second fraction of alkylene oxide from the alkylene oxide rich vapor stream 228 in the second reabsorption section 306 includes reabsorbing more than about 40 percent of the alkylene oxide from the alkylene oxide rich vapor stream 228. In some embodiments, reabsorbing the second fraction of alkylene oxide from the alkylene oxide rich vapor stream 228 in the second reabsorption section 306 includes reabsorbing more than about 20 percent of the alkylene oxide from the alkylene oxide rich vapor stream 228. In certain other embodiments, reabsorbing the second fraction of alkylene oxide from the alkylene oxide rich vapor stream 228 in the second reabsorption section 306 includes reabsorbing more than about 10 percent of the alkylene oxide from the alkylene oxide rich vapor stream 228. As will be appreciated, substantially all of the alkylene oxide from the alkylene oxide rich vapor stream 228 that has not been reabsorbed in the first reabsorption section 304 is reabsorbed as the second fraction in the second reabsorption section 306. As will be appreciated, reabsorbing the second fraction of alkylene oxide from the alkylene oxide rich vapor stream 228 can reabsorb aldehydic impurities that may be present in the alkylene oxide rich vapor stream 228.

In some embodiments, reabsorbing the second fraction of alkylene oxide can occur by contacting a volume of the second water stream 332 and the alkylene oxide rich vapor stream 228. In one embodiment, reabsorbing the first fraction from the alkylene oxide rich vapor stream 228 includes providing about 0.1 percent to about 80 percent of a combined volume of the volume of the first water stream 314 and the volume of the second water stream 332. In some embodiments, reabsorbing the first fraction from the alkylene oxide rich vapor stream 228 includes providing about 0.1 percent to about 60 percent of the combined volume of the first water stream 314 and the second water stream 332.

In the illustrated embodiment of FIG. 3, the second reabsorption section 306 has a second gaseous stream inlet 336 to introduce a second gaseous stream 337 to remove light gases such as carbon dioxide and oxygen from the second aqueous solution 334 to form a second light impurities fraction 338. In some embodiments, the second light impurities fraction 338 that is formed in the second reabsorption section 306 and the first light impurities fraction 322 that is formed in the first reabsorption section 304 flows upward to an upper portion of the column 300. A second outlet 340 is provided on the upper portion of the column 300 within the second reabsorption section 306 to remove the first light impurities fraction 322 and the second light impurities fraction 338. In some embodiments, components of alkylene oxide rich vapor stream 228 that are not reabsorbed at the first reabsorption section 304 and/or the second reabsorption section 306 are removed through the second outlet 340 and can include components such as steam.

The second reabsorption section 306 can additionally include a second take-off 342 located in the second reabsorption section 306 to remove the second aqueous solution 334. In some embodiments, the second take-off 342 is in physical communication with the main glycol unit to transfer the second aqueous solution 334 from the second reabsorption section 306 to the main glycol unit. In certain other embodiments, the second take-off 342 is in physical communication with an alkylene oxide storage tank.

In some embodiments, the second aqueous solution 334 is substantially free of impurities. In certain embodiments, the second aqueous solution 334 has alkylene oxide in the range of about 1 mole percent to about 10 mole percent. In one particular embodiment, the second aqueous solution 334 has ethylene oxide in the range of about 1 mole percent to about 10 mole percent.

An unexpected result of the illustrated embodiment of FIG. 3 is the relatively higher reabsorption of aldehydic impurities at the first reabsorption section 304 when compared to the embodiment illustrated in FIG. 2. A benefit of this unexpected result is that the stream from the second reabsorption section (for example, the second aqueous solution) can be sent directly to a main glycol unit. An added benefit is that a smaller proportion of the reabsorbed alkylene oxide (for example, the first aqueous solution) is sent to a purification column for further processing which may lower production costs.

Figure 4:
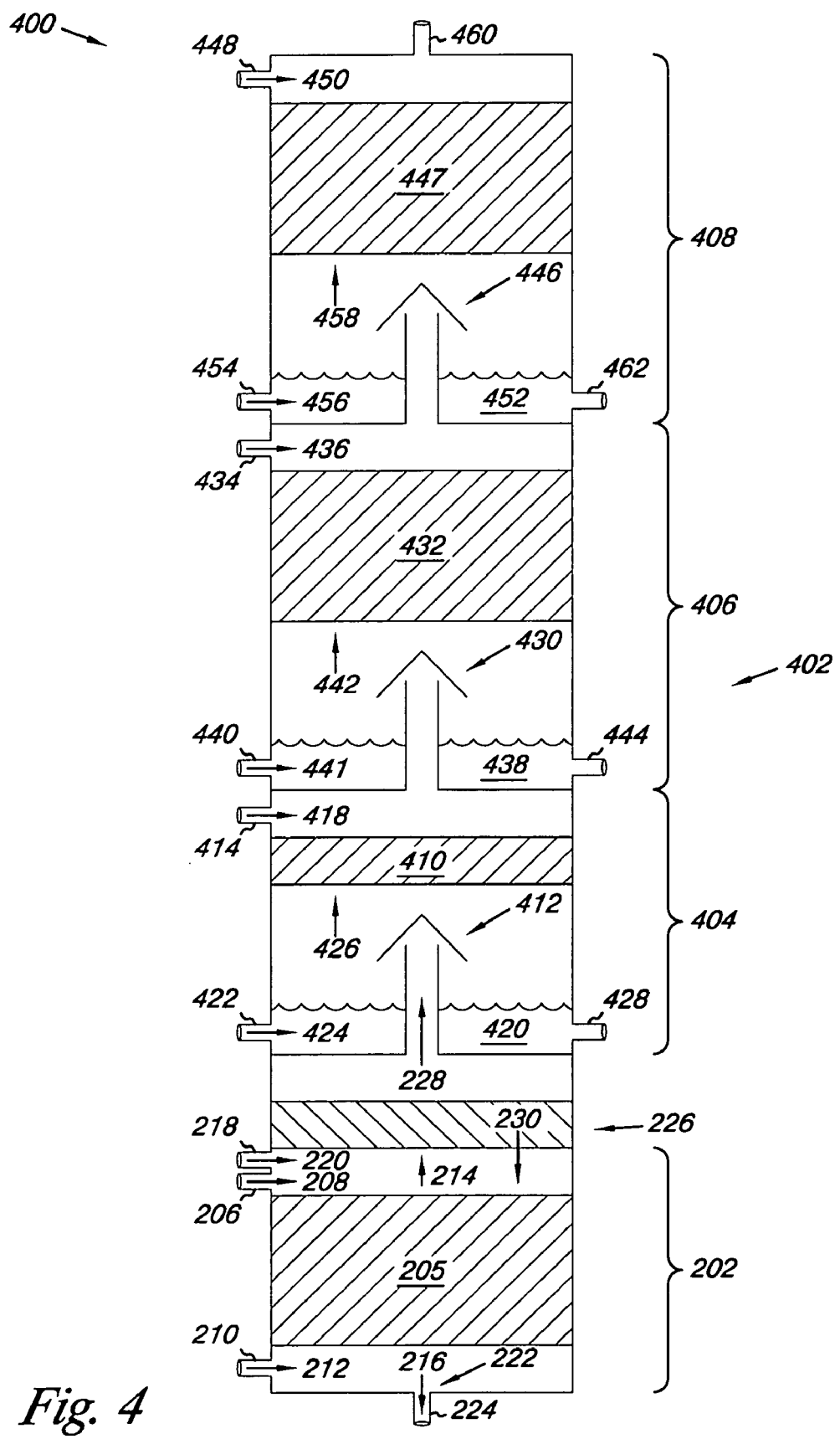
FIG. 4 illustrates an exemplary system for recovery of alkylene oxide in accordance with embodiments of the present invention.

FIG. 4 illustrates an alkylene oxide recovery column 400, in accordance with embodiments of the present invention. The column 400 includes the stripping section 202 and the condenser 226, as described previously with reference to FIG. 2 and FIG. 3.

The first alkylene oxide rich vapor stream 228 exiting the condenser 226 enters a lower portion of a reabsorption region 402 of the column 400. As compared to FIG. 2 and FIG. 3, the reabsorption region 402 of the column 400 includes a third reabsorption section 408 in addition to a first reabsorption section 404 and a second reabsorption section 406.

The first reabsorption section 404, as illustrated in FIG. 4, can have a zone 410 and the zone 410 includes separation stages (e.g., trays, dumped packing, structured packing or a mixture of trays and packing). In one embodiment, the first reabsorption section 404 can be configured in such a way as to include between 1 and 10 separation stages, more preferably between 1 and 8 separation stages, and most preferably between 1 and 6 separation stages.

The temperature of the first reabsorption section 404, in some embodiments can be in the range of about 10° C. to about 120° C., preferably from about 20° C. to about 100° C.,
and more preferably from about 25° C. to about 80° C. The pressure in the first reabsorption section 404 can be in the range of about 60 kilopascal (kPa) to about 2,200 kPa, preferably from about 80 kPa to about 1,100 kPa, and more preferably from about 100 kPa to about 450 kPa.

In some embodiments, the first reabsorption section 404 can include a first chimney tray 412 located at a lower portion of the first reabsorption section 404. As illustrated in FIG. 4, the alkylene oxide rich vapor stream 228 can enter the first reabsorption section 404 through the chimney tray 412.

A first water inlet 414 is provided in the first reabsorption section 404 to introduce a first water stream 418. The first water stream 418 reabsorbs a first fraction of alkylene oxide from the alkylene oxide rich vapor stream 228 to form a first aqueous solution 420 that is collected on the first chimney tray 412. As will be appreciated, reabsorbing the first fraction of alkylene oxide from the alkylene oxide rich vapor stream 228 to form the first aqueous solution 420 can occur by contacting a volume of the first water stream 418 sufficient enough to reabsorb the first fraction. According to embodiments of the present invention, reabsorbing the first fraction of alkylene oxide from the alkylene oxide rich vapor stream 228 in the first reabsorption section 404 includes reabsorbing about 0.1 percent to about 15 percent of the alkylene oxide from the alkylene oxide rich vapor stream 228. In particular embodiments, reabsorbing the first fraction of alkylene oxide from the alkylene oxide rich vapor stream 228 in the first reabsorption section 404 include reabsorbing about 1 percent to about 10 percent of the alkylene oxide from the alkylene oxide rich vapor stream 228. As will be appreciated, reabsorbing the first fraction of alkylene oxide from the alkylene oxide rich vapor stream 228 can reabsorb aldehydic impurities that may be present in the alkylene oxide rich vapor stream 228. In some embodiments, about 20 percent, or more than about 20 percent of the aldehydic impurities present in the alkylene oxide rich vapor stream 228 are reabsorbed as the first fraction. In certain embodiments, about 20 percent to about 40 percent of the aldehydic impurities present in the alkylene oxide rich vapor stream 228 are reabsorbed as the first fraction. In one embodiment, about 40 percent to about 60 percent of the aldehydic impurities present in the alkylene oxide rich vapor stream 228 are reabsorbed as the first fraction. Non-limiting examples of aldehydic impurities include acetaldehyde and formaldehyde.

In some embodiments, the first reabsorption section 404 has a first gaseous stream inlet 422 to introduce a first gaseous stream 424 to remove light gases such as carbon dioxide and oxygen from the first aqueous solution 420 to form a first light impurities fraction 426. In embodiments where the first light impurities fraction 426 are formed, the first light impurities fraction 426 flows upward along with the alkylene oxide rich vapor stream 228 that has not been reabsorbed in the first reabsorption section 404 to the second reabsorption section 406.

In some embodiments, the first aqueous solution 420 has a composition of alkylene oxide in the range of about 0.5 mole percent to about 20 mole percent, acetaldehyde in the range of about 0 mole ppm to about 5,000 mole ppm and formaldehyde in the range of about 0 mole ppm to about 10,000 mole ppm. In one particular embodiment, the first aqueous solution 420 has a composition of ethylene oxide in the range of about 0.5 mole percent to about 20 mole percent, acetaldehyde in the range of about 0 mole ppm to about 5,000 mole ppm and formaldehyde in the range of about 0 mole ppm to about 10,000 mole ppm. The first aqueous solution 420 may further contain compounds that may be typically used and/or formed during alkylene oxide production processes such as chlorine containing organic compounds and oxygenated hydrocarbons.

The first reabsorption section 404 can additionally include a first take-off 428 located in the first reabsorption section 404 to remove the first aqueous solution 420. In certain embodiments, the first take-off off 428 can be located at a side wall of the first reabsorption section 404. In some embodiments, the first take-off 428 is in physical communication with a glycol production unit to transfer the first aqueous solution 420 from the first reabsorption section 404 to the glycol production unit. In certain embodiments, the first take-off 428 is in physical communication with an alkylene oxide purification unit to transfer the first aqueous solution 420 from the first reabsorption section 404 to the alkylene oxide purification unit. The alkylene oxide purification unit can further refine the first aqueous solution 420 to remove impurities such as aldehydic impurities (namely, acetaldehyde and formaldehyde) and/or light gases (namely, carbon dioxide and oxygen).

The alkylene oxide rich vapor stream 228 exiting the first reabsorption section 404 flows downward to a lower portion of the second reabsorption section 406 through a second chimney tray 430. In some embodiments, the temperature in the second reabsorption section 406 is in the range of about 10° C. to about 120° C., preferably from about 20° C. to about 100° C., and more preferably from about 25° C. to about 80° C. The pressure in the second reabsorption section 406 can be in the range of about 60 kilopascal (kPa) to about 2,200 kPa, preferably from about 80 kPa to about 1,100 kPa, and more preferably from about 100 kPa to about 450 kPa.

The second reabsorption section 406 can have a zone 432, where the zone 432 includes separation stages (e.g., trays, dumped packing, structured packing or a mixture of trays and packing). In some embodiments, the second reabsorption section 406 can be configured in such a way as to include between 2 and 10 separation stages, preferably between 3 and 9 separation stages, and more preferably between 4 and 8 separation stages.

A second water inlet 434 is provided in the second reabsorption section 406 to introduce a second water stream 436. The second water stream 436 reabsorbs a second fraction of alkylene oxide from the alkylene oxide rich vapor stream 228 to form a second aqueous solution 438 that is collected on the second chimney tray 430. According to embodiments of the present invention, reabsorbing the second fraction of alkylene oxide from the alkylene oxide rich vapor stream 228 in the second reabsorption section 406 includes reabsorbing about 10 percent to about 80 percent of the alkylene oxide from the alkylene oxide rich vapor stream 228. In some embodiments, reabsorbing the second fraction of alkylene oxide from the alkylene oxide rich vapor stream 228 in the second reabsorption section 406 includes reabsorbing about 15 percent to about 60 percent of the alkylene oxide from the alkylene oxide rich vapor stream 228. As will be appreciated, reabsorbing the second fraction of alkylene oxide from the alkylene oxide rich vapor stream 228 can reabsorb aldehydic impurities that may be present in the alkylene oxide rich vapor stream 228. In some embodiments, about 20 percent, or more than about 20 percent of the aldehydic impurities present in the alkylene oxide rich vapor stream 228 are reabsorbed as the second fraction. In one embodiment, about 20 percent to about 75 percent of the aldehydic impurities present in the alkylene oxide rich vapor stream 228 are reabsorbed as the second fraction. Non-limiting examples of aldehydic impurities include acetaldehyde and formaldehyde.

In the illustrated embodiment of FIG. 4, the second reabsorption section 406 has a second gaseous stream inlet 440 to flow in a second gaseous stream 441 to remove light gases such as carbon dioxide and oxygen from the second aqueous solution 438 to form a second light impurities fraction 442. In some embodiments, the second light impurities fraction 442 that is formed in the second reabsorption section 406 and the first light impurities fraction 426 that is formed in the first reabsorption section 404 flows to the third reabsorption section 408 along with the alkylene oxide rich vapor stream 228.

The second reabsorption section 406 can additionally include a second take-off 444 located in the second reabsorption section 406 to remove the second aqueous solution 438. In some embodiments, the second take-off 444 is in physical communication with a main glycol unit to transfer the second aqueous solution 438 from the second reabsorption section 406 to the main glycol unit. In certain other embodiments, the second take-off 444 is in physical communication with an alkylene oxide storage tank.

In some embodiments, the second aqueous solution 438 is substantially free of impurities. The second aqueous solution 438 has a composition of alkylene oxide in the range of about 1 mole percent to about 10 mole percent. The alkylene oxide rich vapor stream 228 exiting the second reabsorption section 406 enters the third reabsorption section 408.

As illustrated in FIG. 4, the alkylene oxide rich vapor stream 228 can enter the third reabsorption section 408 through a third chimney tray 446. The third reabsorption section 408 can have a zone 447, where the zone 447 includes separation stages (e.g., trays, dumped packing, structured packing or a mixture of trays and packing). In some embodiments, the third reabsorption section 408 can be configured in such a way as to include between 2 and 10 separation stages, preferably between 3 and 9 separation stages, and more preferably between 4 and 8 separation stages.

A third water inlet 448 is provided in the third reabsorption section 408 to introduce a third water stream 450. The third water stream 450 reabsorbs a third fraction of alkylene oxide from the alkylene oxide rich vapor stream 228 to form a third aqueous solution 452 that is collected on the third chimney tray 446. As will be appreciated, reabsorbing the third fraction of alkylene oxide from the alkylene oxide rich vapor stream 228 to form the third aqueous solution 452 includes reabsorbing substantially all of the remaining alkylene oxide from the alkylene oxide rich vapor stream 228.

In some embodiments, reabsorbing the first fraction of the alkylene oxide rich vapor stream 228 includes providing about 1 percent to about 30 percent of a combined volume of the volume of the first water stream 418, the second water stream 436 and the third water stream 450. In certain embodiments, reabsorbing the first fraction of the alkylene oxide rich vapor stream 228 includes providing about 1 percent to about 15 percent of a combined volume of the volume of the first water stream 418, the second water stream 436 and the third water stream 450. In one embodiment, reabsorbing the first fraction of the alkylene oxide rich vapor stream 228 includes providing about 1 percent to about 30 percent of a combined volume of the volume of the first water stream 418, the second water stream 436 and the third water stream 450 and reabsorbing the second fraction of the alkylene oxide rich vapor stream 228 includes providing about 30 percent to about 80 percent of a combined volume of the volume of the first water stream 418, the second water stream 436 and the third water stream 450. In some embodiments, reabsorbing the first fraction of the alkylene oxide rich vapor stream 228 includes providing about 1 percent to about 15 percent of a combined volume of the volume of the first water stream 418, the second water stream 436 and the third water stream 450 and reabsorbing the second fraction of the alkylene oxide rich vapor stream 228 includes providing about 15 percent to about 80 percent of the combined volume of the first water stream 418, the second water stream 436 and the third water stream 450.

The third reabsorption section 408 can have a third gaseous stream inlet 454 to flow in a third gaseous stream 456 to remove light gases such as carbon dioxide and oxygen from the third aqueous solution 452 to form a third light impurities fraction 458. In some embodiments, the third light impurities fraction 458 flows upward to an upper portion of the third reabsorption section 408 along with the first light impurities fraction 426 and the second light impurities fraction 442.

As illustrated in FIG. 4, a second outlet 460 is provided on the upper portion of the third reabsorption section 408 of the column 400 to remove the first light impurities fraction 426, the second light impurities fraction 442 and the third light impurities fraction 458. In some embodiments, components of alkylene oxide rich vapor stream 228 that are not reabsorbed at the first reabsorption section 404, the second reabsorption section 406 and/or the third reabsorption section 408 are removed through the second outlet 460 and can include components such as steam.

In some embodiments, the third aqueous solution 452 is substantially free of impurities. In one embodiment, the third aqueous solution 452 has a composition of alkylene oxide in the range of about 1 mole percent to about 10 mole percent. In certain embodiments, the third aqueous solution 452 has a composition of alkylene oxide in the range of about 2 mole percent to about 8 mole percent. In one particular embodiment, third aqueous solution 452 has a composition of ethylene oxide in the range of about 2 mole percent to about 8 mole percent.

The third reabsorption section 408 can additionally include a third take-off 462 located in the third reabsorption section 408 to remove the third aqueous solution 452 from the third reabsorption section 408. In certain embodiments, the third take-off 462 can be located at a side wall of the third reabsorption section 408. In some embodiments, the third take-off 462 is in physical communication with the main glycol unit to transfer the third aqueous solution 452 from the third reabsorption section 408 to the main glycol unit. In certain embodiments, the third take-off 462 is in physical communication with the alkylene oxide storage unit to transfer the third aqueous solution 452 from the third reabsorption section 408 to the alkylene oxide storage unit.

An unexpected result of the illustrated embodiment of FIG. 4 is the removal of aldehydic impurities to a certain extent at the first reabsorption section. A benefit of this unexpected result is that the impurities are reduced at the subsequent reabsorption section, the second reabsorption section and as a result the resultant stream from the second reabsorption section (for example, the second aqueous solution) can be sent directly to the main glycol unit. An added benefit when compared to embodiment illustrated in FIG. 3 is that the proportion of the reabsorbed alkylene oxide (for example, the first aqueous solution 334) sent to the purification column for processing is reduced which may lower production costs. The stream from the third reabsorption section (for example, the second aqueous solution) can be sent directly to the main glycol unit or to the alkylene oxide storage unit.

Figure 5:
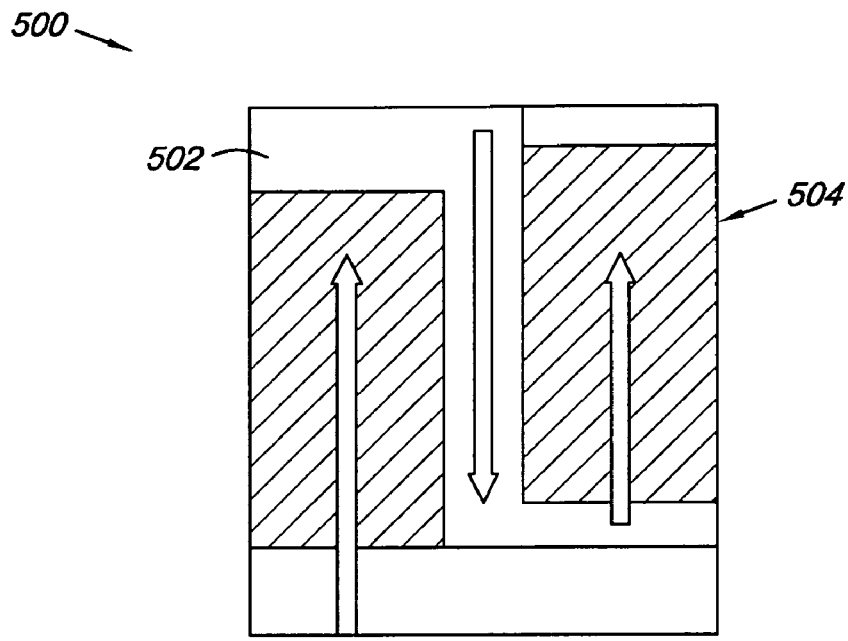
FIG. 5 is a configuration of a reabsorption region according to some embodiments of the invention.

FIG. 5 illustrates an exemplary configuration of a reabsorption region 500, where a first reabsorption section 502 and a second reabsorption section 504 are in a side-by-side fashion. The first reabsorption section 502 is in series with the second reabsorption section 504 and is placed adjacent to each other in a recovery column. An alkylene oxide rich vapor stream entering the reabsorption region 500 can enter the first reabsorption section 502 before flowing into the second reabsorption section 504. In one embodiment, the alkylene oxide rich vapor stream can enter the second reabsorption section 504 before flowing into the first reabsorption section 502. The columns 200, 300 and 400 as illustrated in FIGS. 2, 3, and 4 can include the reabsorption region 500 where the first reabsorption section 502 and the second reabsorption section 504 are arranged in a side-by-side fashion.

Figure 6:
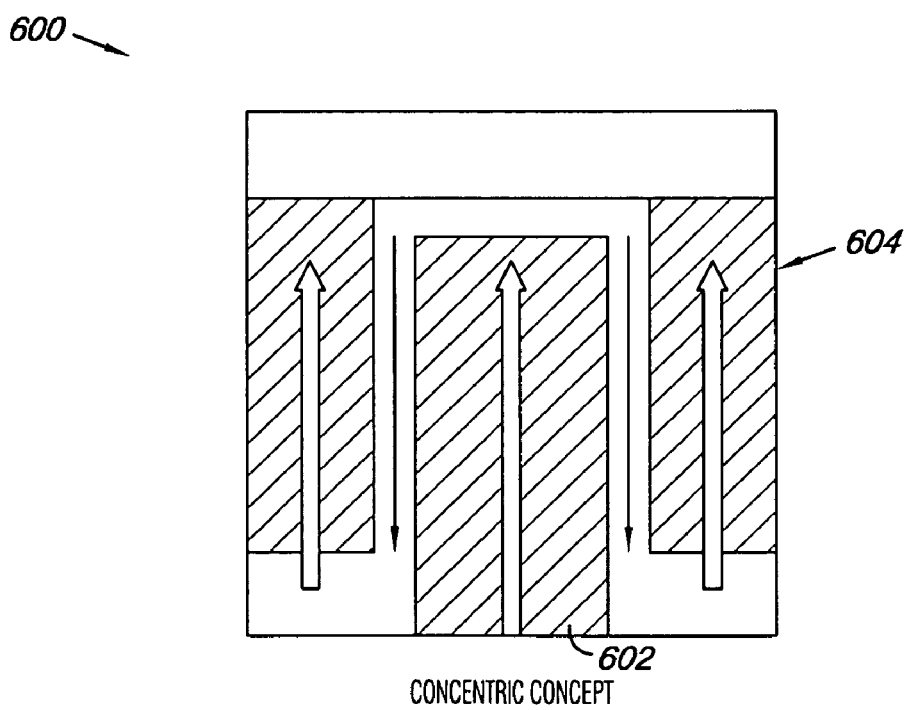
FIG. 6 is a configuration of a reabsorption region according to some embodiments of the invention.

An exemplary configuration of a reabsorption region 600 is illustrated in FIG. 6, where a first reabsorption section 602 and a second reabsorption section 604 are in a side-by-side fashion. An alkylene oxide rich vapor stream entering the reabsorption region 600 can enter the first reabsorption section 602 before flowing into the second reabsorption section 604. In this configuration, the first reabsorption section 602 is concentric with the second reabsorption section 604 and is in series. The columns 200, 300, and 400 as illustrated in FIGS. 2, 3, and 4 can include the reabsorption region 600 where the first reabsorption section 602 and the second reabsorption section 604 are arranged in a side-by-side fashion with a concentric configuration.

As will be appreciated, placing the first reabsorption sections (502, 602) and the second reabsorption sections (504, 604) in a side-by-side fashion may advantageously decrease the size of the recovery columns and may lower the installation cost, capital cost as well as alkylene oxide production costs. In certain embodiments, in addition to the first reabsorption section and the second reabsorption section, the third reabsorption section may also be arranged in a side-by-side fashion.

For the various embodiments, the ethylene oxide recovery according to the present disclosure can be processed to provide further downstream products, such as, for example, 1,2-diols, 1,2-diol ethers, 1,2-carbonates, and alkanolamines. Since the present disclosure provides improvements to the separation and purity of the ethylene oxide, it is contemplated that the improvements provided herein will carry forward to provide improvements to these downstream processes and/or products. Improved methods for the production of 1,2-diols, 1,2-carbonates, 1,2-diol ethers and alkanolamines are thus also provided herein.

The conversion of ethylene oxides into 1,2-diols or 1,2-diol ethers may comprise, for example, reacting the ethylene oxide with water, suitably in the presence of an acidic or basic catalyst. For example, for preferential production of the 1,2-diol over the 1,2-diol ether, the ethylene oxide may be reacted with a tenfold molar excess of water, in a liquid phase reaction in the presence of an acid catalyst, e.g., 0.5-1.0 wt % sulfuric acid, based on the total reaction mixture, at 50-70° C. at 1 bar absolute, or in a gas phase reaction, at 130-240° C. and 20-40 bar absolute, preferably in the absence of a catalyst. If the proportion of water is lowered, the proportion of the 1,2-diol ethers in the reaction mixture will be increased. The 1-2, diol ethers thus produced may comprise di-ethers, tri-ethers, tetra-ethers or other multi-ethers. Alternatively, 1,2-diol ethers may be prepared by converting the ethylene oxide with an alcohol, such as methanol or ethanol, or by replacing at least a portion of the water with the alcohol. The resulting 1,2-diols and diol ethers may be utilized in a wide variety of end-use applications in the food, beverage, tobacco, cosmetic, thermoplastic polymer, curable resin system, detergent, heat transfer system, etc., industries.

The conversion of ethylene oxide recovered according to the present disclosure into alkanolamines may comprise, for example, reacting the ethylene oxide with ammonia. Anhydrous or aqueous ammonia may be used, although anhydrous ammonia favors the production of monoalkanolamine, and may be used when the same is preferred. The resulting alkanolamines may be used, for example, in the treatment of natural gas. The olefin oxide may be converted into the corresponding 1,2-carbonate by reacting the olefin oxide with carbon dioxide. If desired, a 1,2-diol may be prepared by subsequently reacting the 1,2-carbonate with water or an alcohol to form the 1,2-diol. For applicable methods, reference is made to U.S. Pat. No. 6,080,897, which is incorporated herein by reference.

Without further elaboration, it is believed that one skilled in the art can, using the description herein, utilize the present invention to its fullest extent. The following examples are included to provide additional guidance to those skilled in the art in practicing the claimed invention. The examples provided are merely representative of the work that contributes to the teaching of the present application. Accordingly, these examples are not intended to limit the invention, as defined in the appended claims, in any manner.

SPECIFIC EMBODIMENTS OF THE PRESENT DISCLOSURE

Example 1

Mass and energy balances are performed on the column 100 illustrated in FIG. 1 using Aspenplus® Release 2004.1 from Aspen Technology, Inc. (Cambridge, Mass. USA), a commercially available simulation package. The components present in a typical ethylene oxide/ethylene glycol production unit such as ethylene oxide, ethylene, oxygen, argon, carbon dioxide, methane, water, ethane, nitrogen, monoethylene glycol, diethylene glycol, triethylene glycol, tetraethylene glycol, acetaldehyde and formaldehyde are considered. The base method used in the simulation is the UNIQUAC/Redlich-Kwong equation of state with Henry's Law. The reabsorption portion of the column 100 is modeled using a single six-separation stage RadFrac block. The water stream is fed at separation stage 1, the uppermost separation stage of the RadFrac block and the ethylene oxide rich vapor stream is fed at separation stage 5. The steam stream is fed at the lowermost separation stage, separation stage 6 to remove light gases and the second aqueous solution exits at the base of separation stage 6 after removal of the light gases. The light impurity fraction exits at the top part of the separation stage 1. In the simulation, the flow of the water stream and heat inputs to the first stripping portion are adjusted to give the desired concentration of the light gases and concentration of ethylene oxide in the second aqueous solution. The simulation resulted in values expressed as kilograms per hour (kg/hr) as shown in Table 1.

TABLE 1

| (kg/hr) | ethylene oxide rich vapor stream | water stream | Second aqueous solution |
|---|---|---|---|
| ethylene oxide | 46913 | 0 | 46913 |
| acetaldehyde | 4.2 | 0 | 4.2 |
| formaldehyde | 2.8 | 0 | 2.8 |
| water | 917 | 429673 | 434710 |

Example 2

Mass and energy balances are performed on the column 200 illustrated in FIG. 2 using Aspenplus® Release 2004.1 from Aspen Technology, Inc., Cambridge, Mass., as in the previous example. In Example 1, the reabsorption region of the column 200 is modeled using two RadFrac blocks, a first RadFrac block that corresponds to the first reabsorption section with 2 separation stages and a second RadFrac block that corresponds to the second reabsorption section with 6 separation stages. The first water stream is fed at the uppermost separation stage, separation stage 1, of the first RadFrac block and the ethylene oxide rich vapor stream 228 is introduced at separation stage 2 of the first RadFrac block. The first aqueous solution is removed from the base of separation stage 2 of the first RadFrac block. The ethylene oxide rich vapor stream that has not been reabsorbed at the first reabsorption section exits at separation stage 1 of the first RadFrac block. The second reabsorption section of the Example 2 is modeled in the same fashion as the reabsorption portion of the Example 1. The second water stream is fed at separation stage 1, the uppermost separation stage of the second RadFrac block and the ethylene oxide vapor stream is fed at separation stage 5 of the second RadFrac block. The second gaseous stream is fed at the lowermost separation stage, separation stage 6 to remove light gases and the second aqueous solution exits the base of separation stage 6 after removal of the light gases. The second light impurities fraction exits at the top part of the separation stage 1. In the simulation, flow of the first and second water streams and heat inputs to the stripping section are adjusted to give the desired concentration of the second light impurities fraction and concentration of ethylene oxide in the respective first and second aqueous solutions. The simulation resulted in values as shown in Table 2.

TABLE 2

| (kg/hr) | first water stream | first aqueous solution | second water stream | second aqueous solution |
|---|---|---|---|---|
| ethylene oxide | 0 | 1008 | 0 | 45905 |
| acetaldehyde | 0 | 0.2 | 0 | 4.0 |
| formaldehyde | 0 | 2.7 | 1.7 | 1.7 |
| water | 5000 | 4844 | 431814 | 437007 |

The formaldehyde impurity to a large extent is reabsorbed in the first aqueous solution as a result the concentration of formaldehyde in the second aqueous solution is minimized. The second aqueous solution of Example 2, in comparison, to the second aqueous solution of Example 1, has lower content of impurities such as acetaldehyde and formaldehyde due to the presence of the second reabsorption section in the recovery column 200.

Example 3

Mass and energy balances are performed on the column 300 illustrated in FIG. 3 using Aspenplus® Release 2004.1 from Aspen Technology, Inc., Cambridge, Mass., as in the previous examples. The reabsorption region of the column 300 is modeled using two RadFrac blocks, a first RadFrac block that corresponds to the first reabsorption section with 6 separation stages and a second RadFrac block that corresponds to the second reabsorption section with 6 separation stages. In the first RadFrac block, the first water stream is fed at separation stage 1, the uppermost separation stage of the first RadFrac block and the ethylene oxide vapor stream is fed at separation stage 5. The first gaseous stream is fed at the lowermost separation stage, separation stage 6, to remove light gases, and the first aqueous solution exits the base of separation stage 6 of the first RadFrac block after removal of the light gases. The first light impurities fraction exits at the top part of the separation stage 1. In the second RadFrac block, the second water stream is introduced at separation stage 1, the uppermost separation stage of the second RadFrac block, and the ethylene oxide vapor stream is fed at separation stage 5. The second gaseous stream is introduced at the lowermost separation stage, separation stage 6 to remove the light gases and the second aqueous solution exits the base of separation stage 6 after removal of the light gases. The second light impurities fraction exits at the top part of the separation stage 1. In the simulation, the flow of the first water stream, the second water stream and heat inputs to the stripping section are adjusted to give the desired concentration of the first and second light impurities fractions and concentration of ethylene oxide in the respective first and second aqueous solutions. The simulation resulted in values as shown in Table 3.

TABLE 3

| (kg/hr) | first water stream | first aqueous solution | second water stream | second aqueous solution |
|---|---|---|---|---|
| ethylene oxide | 0 | 32127 | 0 | 14785 |
| acetaldehyde | 0 | 3.9 | 0 | 0.3 |
| formaldehyde | 0 | 2.8 | 0 | 0 |
| water | 255011 | 256073 | 217424 | 223381 |

The formaldehyde and acetaldehyde impurities to a larger extent are reabsorbed in the first aqueous solution as a result the concentration of formaldehyde and acetaldehyde in the second aqueous solution is minimized. The second aqueous solution of Example 3, in comparison, to the second aqueous solution of Example 2, has lower content of impurities such as acetaldehyde and formaldehyde. The reduction of impurities to a greater extent at the second reabsorption section of the column 300 is due to the greater number of separation stages in the second reabsorption section as compared to the second reabsorption section of Example 2.

Example 4

Mass and energy balances are performed on the column 400 illustrated in FIG. 4 using Aspenplus® Release 2004.1 from Aspen Technology, Inc., Cambridge, Mass., as in the previous examples. The reabsorption region of the column 400 is modeled using three RadFrac blocks, a first RadFrac block that corresponds to the first reabsorption section with 2 separation stages, a second RadFrac block that corresponds to the second reabsorption section with 6 separation stages and a third RadFrac block that corresponds to the third reabsorption section with 6 separation stages. In the first RadFrac block corresponding to the first reabsorption section, the first water stream is fed at the uppermost separation stage, separation stage 1, and the ethylene oxide rich vapor stream 228 is introduced at separation stage 2. The first aqueous solution is removed from the base of separation stage 2 of the first RadFrac block. The ethylene oxide rich vapor stream that has not been reabsorbed at the first reabsorption section exits at separation stage 1 of the first RadFrac block. In the second RadFrac block, the second water stream is fed at separation stage 1, the uppermost separation stage of the second RadFrac block and the ethylene oxide vapor stream is fed at separation stage 5. The second gaseous stream is fed at the lowermost separation stage, separation stage 6, to remove light gases and the second aqueous solution exits the base of separation stage 6 of the second RadFrac block after removal of the light gases. The second light impurities fraction exits at the top part of the separation stage 1. In the third RadFrac block, the third water stream is introduced at separation stage 1, the uppermost separation stage of the third RadFrac block, and the ethylene oxide vapor stream is fed at separation stage 5. The third gaseous stream is introduced at the lowermost separation stage, separation stage 6 to remove the light gases and the third aqueous solution exits the base of separation stage 6 after removal of the light gases. In the simulation, flows of the first water stream, the second water stream and the third water stream as well as heat inputs to the stripping section are adjusted to give desired concentrations of the second and third light impurities fractions and concentration of ethylene oxide in the respective first aqueous solution, the second aqueous solution and the third aqueous solution. The simulation resulted in values as shown in Table 4.

TABLE 4

| (kg/hr) | first water stream | First aqueous solution | second water stream | second aqueous solution | third water stream | Third aqueous solution (kg/hr) |
|---|---|---|---|---|---|---|
| ethylene oxide | 2.4 | 409 | 0 | 31195 | 0 | 15317 |
| acetaldehyde | 0 | 0.1 | 0 | 3.8 | 0 | 0.3 |
| formaldehyde | 0 | 2.6 | 0 | 0.2 | 0 | 0 |
| water | 1948 | 1899 | 255011 | 256073 | 217424 | 223576 |

The formaldehyde impurity to a large extent is reabsorbed in the first reabsorption section and the remaining formaldehyde impurity present in the ethylene oxide rich vapor stream is reabsorbed in the second reabsorption section. The acetaldehyde impurity to a large extent is reabsorbed in the second reabsorption section as a result the third aqueous solution is substantially free of impurities. Due to the presence of three reabsorption sections in column 400 volume of aqueous solutions generated at each of the reabsorption sections is lower when compared to the single reabsorption section. An additional benefit of Example 4 is that according to the impurity content of each of the aqueous solutions they may be processed individually as opposed to processing a larger volume of the first aqueous solution, as in Example 1 and this may reduce the cost of operations.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:
1. A process for recovery of alkylene oxide comprising:
introducing a feed stream containing alkylene oxide to a stripping section of an alkylene oxide recovery column, wherein the alkylene oxide recovery column comprises the stripping section and a reabsorption region;
stripping alkylene oxide from the feed stream to form a first gaseous portion in the stripping section, wherein the first gaseous portion flows from the stripping section to the reabsorption region of the alkylene oxide recovery col- umn, and wherein the reabsorption region further comprises a first reabsorption section and a second reabsorption section;

partially condensing the first gaseous portion into a liquid reflux stream and an alkylene oxide rich vapor stream, wherein the liquid reflux stream is in physical communication with the stripping section;

reabsorbing a first fraction of the alkylene oxide rich vapor stream in a first water stream to form a first aqueous solution in the first reabsorption section, wherein the first reabsorption section further comprises a first take-off to remove the first aqueous solution from the first reabsorption section; and reabsorbing a second fraction of the alkylene oxide rich vapor stream in a second water stream to form a second aqueous solution in the second reabsorption section, wherein the second reabsorption section further comprises a second take-off to remove the second aqueous solution from the second reabsorption section.

2. The process of claim 1, further comprising reabsorbing a third fraction of the alkylene oxide rich vapor stream in a third water stream to form a third aqueous solution in a third reabsorption section, wherein the third reabsorption section further comprises a third take-off to remove the third aqueous solution from the third reabsorption section, and wherein the reabsorption region of the alkylene oxide recovery column comprises the first reabsorption section, the second reabsorption section and the third reabsorption section.

3. The process of claim 2, further comprising stripping light gases from at least one of the first aqueous solution, the second aqueous solution and the third aqueous solution by introducing a gaseous stream to form a light impurities fraction, wherein the light impurities fraction is removed from the alkylene oxide recovery column through an outlet at an upper portion of the alkylene oxide recovery column.

4. The process of claim 1, wherein at least one of the second aqueous solution and the third aqueous solution is substantially free of impurities.

5. The process of claim 2, wherein reabsorbing the first fraction of the alkylene oxide rich vapor stream in the first water stream comprises reabsorbing about 0.1 percent to about 15 percent of the alkylene oxide from the alkylene oxide rich vapor stream, and wherein reabsorbing the second fraction of the alkylene oxide rich vapor stream in the second water stream comprises reabsorbing about 10 percent to about 80 percent of the alkylene oxide from the alkylene oxide rich vapor stream.

6. The process of claim 1, further comprising introducing at least one input stream comprising alkylene oxide, or alkylene or both in the stripping section from a pre-recovery process or a post-recovery process or both, wherein the at least one input stream and the feed stream are stripped in the stripping section.

7. The process of claim 1, wherein reabsorbing the first fraction of the alkylene oxide rich vapor stream in the first water stream comprises reabsorbing about 0.1 percent to about 80 percent of the alkylene oxide from the alkylene oxide rich vapor stream.

8. The process of claim 7, wherein reabsorbing the first fraction of the alkylene oxide rich vapor stream in the first water stream comprises reabsorbing about 0.1 percent to about 15 percent of the alkylene oxide from the alkylene oxide rich vapor stream.

9. The process of claim 1, wherein reabsorbing the first fraction of the alkylene oxide rich vapor stream in the first water stream comprises providing about 0.1 percent to about 80 percent of the combined volume of the first water stream and the second water stream.

10. The process of claim 1, wherein the alkylene oxide is one of ethylene oxide or propylene oxide.

11. A system for recovery of alkylene oxide comprising:
a stripping section located in an alkylene oxide recovery column to convert a portion of a feed stream to a gas phase portion, wherein the gas phase portion of the feed stream comprises alkylene oxide;
a condenser to partially condense the gas phase portion of the feed stream to produce an alkylene oxide rich vapor stream and a liquid reflux stream;
a first reabsorption section in the alkylene oxide recovery column to reabsorb in a first water stream a first fraction of the alkylene oxide from the alkylene oxide rich vapor stream to form a first aqueous solution, wherein the first reabsorption section comprises a first water inlet to provide the first water stream; and
a second reabsorption section in the alkylene oxide recovery column to reabsorb in a second water stream a second fraction of the alkylene oxide from the alkylene oxide rich vapor stream to form a second aqueous solution, wherein the second reabsorption section comprises a second water inlet to provide the second water stream.

12. The system of claim 11, further comprising a third reabsorption section in the alkylene oxide recovery column to reabsorb in a third water stream a third fraction of the alkylene oxide from the alkylene oxide rich vapor stream to form a third aqueous solution, wherein the third reabsorption section comprises a third water inlet to provide the third water stream.

13. The system of claim 11, wherein the stripping section further comprises at least one inlet to provide at least one input stream comprising alkylene or alkylene oxide or both from a pre-recovery process or a post-recovery process or both, wherein the at least one input stream and the feed stream are stripped in the stripping section.

14. The system of claim 13, further comprising at least one gaseous stream inlet to provide at least one gaseous stream to at least one of the first reabsorption section, the second reabsorption section and the third reabsorption section to strip light gases from at least one of the first aqueous solution, the second aqueous solution and the third aqueous solution to form a light impurities fraction; and
a second outlet at an upper portion of the alkylene oxide recovery column to remove the light impurities fraction from the alkylene oxide recovery column.

15. The system of claim 11, wherein the condenser is located at an upper portion of the stripping portion integral to the alkylene oxide recovery column, or wherein the condenser is located external to the alkylene oxide recovery column.

16. The system of claim 11, wherein the second reabsorption section is located in a side-by-side fashion with the first reabsorption section.

17. The system of claim 11, further comprising at least one chimney tray located at at least one of the first reabsorption section, the second reabsorption section and the third reabsorption section, wherein at least one of the first aqueous solution, the second aqueous solution and the third aqueous solution are collected on the chimney tray while the alkylene oxide rich vapor stream passes through the chimney tray.

18. The system of claim 11, further comprising at least one take-off located at a lower portion of at least one of the first reabsorption section, the second reabsorption section and the third reabsorption section to remove at least one of the first aqueous solution, the second aqueous solution and the third aqueous solution.

19. The system of claim 18, wherein the at least one take-off located at the lower portion of at least one of the second reabsorption section and the third reabsorption section is in physical communication with a main glycol unit.

20. A system for recovery of alkylene oxide comprising:
a stripping section located in an alkylene oxide recovery column to convert a portion of a feed stream to a gas phase portion, wherein the gas phase portion of the feed stream comprises alkylene oxide, and wherein the alkylene oxide is ethylene oxide;
a condenser to partially condense the gas phase portion of the feed stream to produce an alkylene oxide rich vapor stream and a liquid reflux stream;
a first reabsorption section in the alkylene oxide recovery column to reabsorb in a first water stream a first fraction of the alkylene oxide from the alkylene oxide rich vapor stream to form a first aqueous solution, the first reabsorption section further comprising a first water inlet to provide the first water stream to reabsorb about 0.1 percent to about 15 percent of the alkylene oxide from the alkylene oxide rich vapor stream;
a second reabsorption section in the alkylene oxide recovery column to reabsorb in a second water stream a second fraction of the alkylene oxide from the alkylene oxide rich vapor stream to form a second aqueous solution, the second reabsorption section further comprising a second water inlet to provide the second water stream to reabsorb about 10 percent to about 80 percent of the alkylene oxide from the alkylene oxide rich vapor stream; and
a third reabsorption section in the alkylene oxide recovery column to reabsorb in a third water stream a third fraction of the alkylene oxide from the alkylene oxide rich vapor stream to form a third aqueous solution, wherein the third aqueous solution is substantially free of impurities.

* * * * *